(12) United States Patent
Vandenbossche et al.

(10) Patent No.: US 6,475,247 B1
(45) Date of Patent: Nov. 5, 2002

(54) NAPHTHALENE CATIONIC COUPLER FOR OXIDATION DYEING OF KERATIN FIBER

(75) Inventors: Jean-Jacques Vandenbossche, Tartas; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/646,642

(22) PCT Filed: Jan. 19, 2000

(86) PCT No.: PCT/FR00/00060
§ 371 (c)(1),
(2), (4) Date: Nov. 22, 2000

(87) PCT Pub. No.: WO00/42980
PCT Pub. Date: Jul. 27, 2000

(30) Foreign Application Priority Data

Jan. 21, 1999 (FR) .............................. 99/00637

(51) Int. Cl.$^7$ ................................. A61K 7/13
(52) U.S. Cl. ................ 8/405; 8/405; 8/406; 8/407; 8/410; 8/412; 8/423; 548/400
(58) Field of Search ............ 8/405, 406, 407, 8/410, 412, 421, 423; 548/400

(56) References Cited

U.S. PATENT DOCUMENTS

| | | | | |
|---|---|---|---|---|
| 4,823,985 A | | 4/1989 | Grollier et al. ................. | 222/1 |
| 5,061,289 A | | 10/1991 | Clausen et al. ................. | 8/409 |
| 5,380,340 A | | 1/1995 | Neunhoeffer et al. .......... | 8/409 |
| 5,766,576 A | | 6/1998 | Löwe et al. .................... | 422/62 |
| 5,769,903 A | * | 6/1998 | Audousset et al. ............. | 8/409 |
| 5,849,041 A | * | 12/1998 | Kunz et al. ..................... | 8/408 |
| 6,099,593 A | | 8/2000 | Terranova et al. .............. | 8/409 |

FOREIGN PATENT DOCUMENTS

| | | |
|---|---|---|
| DE | 38 43 892 | 6/1990 |
| DE | 41 33 957 | 4/1993 |
| DE | 195 43 988 | 5/1997 |
| EP | 1063399 | * 3/1967 |
| FR | 1 460 145 | 2/1967 |
| FR | 1 533 643 | 11/1968 |
| FR | 2 586 913 | 3/1987 |
| FR | 2 733 749 | 11/1996 |
| GB | 1 026 978 | 4/1966 |
| GB | 1 153 196 | 5/1969 |
| GB | 2 750 048 | 12/1997 |
| JP | 61-267059 | 11/1986 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |

OTHER PUBLICATIONS

English lauguage Derwent Abstract of FR 2 733 749.
English language Derwent Abstract of JP 61–267059.
English language Derwent Abstract of JP 2–19576.
English language Derwent Abstract of JP 9–110659.
George M. Sieger et al., "Dialkylaminoalkyl Esters and Amides Derived from 3–Hydroxy–and 3–Alkoxy–2–naphthoic Acids", Journal of the American Pharmaceutical Association, vol. XLVII, No. 10, Oct. 1958, pp. 734–744.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The invention relates to a composition for the oxidation dyeing of keratin fibers, and in particular of human keratin fibers such as the hair, comprising at least one oxidation base and, as coupler, at least one 2-hydroxynaphthalene of formula (I) comprising at least one cationic group Z of formula (II), to their use as couplers for the oxidation dyeing of keratin fibers, to oxidation dyeing processes using them and to novel cationic 2-hydroxynaphthalenes of formula (I').

73 Claims, No Drawings

NAPHTHALENE CATIONIC COUPLER FOR OXIDATION DYEING OF KERATIN FIBER

The invention relates to a composition for the oxidation dyeing of keratin fibres, and in particular of human keratin fibres such as the hair, comprising at least one oxidation base and, as coupler, at least one 2-hydroxynaphthalene of formula (I) comprising at least one cationic group Z of formula (II), to their use as couplers for the oxidation dyeing of keratin fibres, to oxidation dyeing processes using them and to novel cationic 2-hydroxynaphthalenes of formula (I').

It is known practice to dye keratin fibres, and in particular human hair, with dye compositions containing oxidation dye precursors, in particular para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols, non-cationic naphthols or certain heterocyclic compounds such as, for example, indole couplers.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

Now, the Applicant has just discovered, entirely surprisingly and unexpectedly, that novel cationic 2-hydroxynaphthalenes of formula (I) defined below, comprising at least one cationic group Z, Z being chosen from quaternized aliphatic chains, aliphatic chains comprising at least one quaternized saturated ring and aliphatic chains comprising at least one quaternized unsaturated ring, are not only suitable for use as couplers for oxidation dyeing, but also allow dye compositions to be obtained which lead to strong colorations, in a wide range of shades, and which have excellent properties of resistance to the various treatments to which keratin fibres may be subjected.

These discoveries form the basis of the present invention.

A first subject of the invention is thus a composition for the oxidation dyeing of keratin fibres, and in particular of human keratin fibres such as the hair, characterized in that it contains, in a medium which is suitable for dyeing:
at least one oxidation base, and
at least one coupler chosen from the compounds of formula (I) below, and the addition salts thereof with an acid:

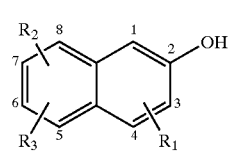

(I)

in which:

$R_1$, $R_2$ and $R_3$, which may be identical or different, represent a hydrogen atom; a halogen atom; a group Z as defined below; a ($C_1$–$C_6$)alkylcarbonyl radical; an amino($C_1$–$C_6$)alkylcarbonyl radical; an N—Z-amino ($C_1$–C6)alkylcarbonyl radical; an N—($C_1$–$C_6$) alkylamino($C_1$–$C_6$)alkylcarbonyl radical; an N,N-di ($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; a carboxyl radical; a ($C_1$–$C_6$)alkylcarboxyl radical; a $C_1$–$C_6$alkylsulphonyl radical; an aminosulphonyl radical; an N—Z-aminosulphonyl radical; a $C_1$–$C_6$N-alkylaminosulphonyl radical; an N,N-di($C_1$–$C_6$) alkylaminosulphonyl radical; a $C_1$–$C_6$aminosulphonylalkyl radical; a $C_1$–$C_6$N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$alkyl radical; a $C_1$–$C_6$monohydroxyalkyl radical; a $C_2$–$C_6$polyhydroxyalkyl radical; a ($C_1$–$C_6$)alkoxy ($C_1$–$C_6$)alkyl radical; a $C_1$–$C_6$trifluoroalkyl radical; a cyano radical; a group $OR_4$ or $SR_4$; an amino group protected with a ($C_1$–$C_6$)alkylcarbonyl, ($C_1$–$C_6$) alkylcarboxyl, trifluoro($C_1$–$C_6$)alkylcarbonyl, amino ($C_1$–$C_6$)alkylcarbonyl, N—Z-amino($C_1$–$C_6$) alkylcarbonyl, N—($C_1$–$C_6$) alkylamino($C_1$–$C_6$) alkylcarbonyl, N,N-di($C_1$–$C_6$)alkylamino($C_1$–$C_6$) alkylcarbonyl, ($C_1$–$C_6$)alkylcarboxyl, carbamyl, N—($C_1$–$C_6$)alkylcarbamyl, N,N-di($C_1$–$C_6$) alkylcarbamyl, $C_1$–$C_6$alkylsulphonyl, aminosulphonyl, N—Z-aminosulphonyl, $C_1$–$C_6$N-alkylaminosulphonyl, N,N-di($C_1$–$C_6$)alkylaminosulphonyl, thiocarbamyl or formyl radical, or with a group Z as defined below in which the linker arm D contains a ketone function directly linked to the nitrogen atom of the said amino group; a $C_1$–$C_6$aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two identical or different radicals chosen from alkyl, $C_1$–$C_6$monohydroxyalkyl, $C_2$-$C_6$ polyhydroxyalkyl, ($C_1$–$C_6$)alkylcarbonyl, carbamyl, N—($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from the groups Z as defined below, or which can form, together with the nitrogen atom to which they are attached, a 5- or 6-membered carbon-based ring or a ring containing one or more hetero atoms;

$R_4$ denotes a $C_1$–$C_6$alkyl radical; a $C_1$–$C_6$monohydroxyalkyl radical; a $C_2$–$C_6$polyhydroxyalkyl radical; a group Z as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$trifluoroalkyl radical; a $C_1$–$C_6$aminosulphonylalkyl radical; a $C_1$–$C_6$N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; a $C_1$–$C_6$aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two identical or different radicals chosen from $C_1$–$C_6$alkyl, $C_1$–$C_6$monohydroxyalkyl, $C_2$–$C_6$polyhydroxyalkyl, ($C_1$–$C_6$)alkylcarbonyl, formyl, trifluoro($C_1$–$C_6$) alkylcarbonyl, ($C_1$–$C_6$)alkylcarboxyl, carbamyl, N—($C_1$–$C_6$)alkylcarbamyl, N,N-di($C_1$–$C_6$) alkylcarbamyl, thiocarbamyl and $C_1$–$C_6$alkylsulphonyl radicals or from the groups Z as defined below; or which can form, together with the nitrogen atom to which they are attached, a 5- or 6-membered carbon-based ring or a ring containing one or more hetero atoms;

Z is chosen from the unsaturated cationic groups of formulae (II) and (III) below, and the saturated cationic groups of formula (IV) below:

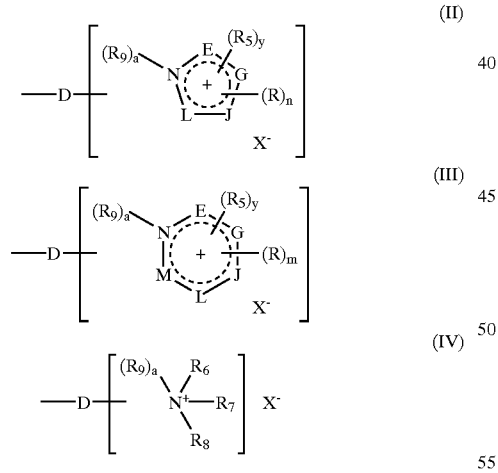

in which:
D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1$–$C_6$alkoxy radicals, and which can bear one or more ketone functions;
the ring members E, G, J, L and M, which may be identical or different, represent a carbon, oxygen, sulphur or nitrogen atom;

n is an integer between 0 and 4 inclusive;
m is an integer between 0 and 5 inclusive;
the radicals R, which may be identical or different, represent a second group Z which is identical to or different from the first group Z, a halogen atom, a hydroxyl radical, a $C_1$–$C_6$alkyl radical, a $C_1$–$C_6$monohydroxyalkyl radical, a $C_2$–$C_6$polyhydroxyalkyl radical, a nitro radical, a cyano radical, a cyano($C_1$–$C_6$)alkyl radical, a $C_1$–$C_6$alkoxy radical, a tri($C_1$–$C_6$)alkylsilane ($C_1$–$C_6$)alkyl radical, an amido radical, an aldehydo radical, a carboxyl radical, a ($C_1$–$C_6$)alkylcarbonyl radical, a thio radical, a $C_1$–$C_6$thioalkyl radical, a $C_1$–$C_6$alkylthio radical, an amino radical, an amino radical protected with a ($C_1$–$C_6$)alkylcarbonyl, carbamyl or $C_1$–$C_6$alkylsulphonyl radical; a group NHR" or NR"R'" in which R" and R'", which may be identical or different, represent a $C_1$–$C_6$alkyl radical, a $C_1$–$C_6$monohydroxyalkyl radical or a $C_2$–$C_6$polyhydroxyalkyl radical;

$R_5$ represents a $C_1$–$C_6$alkyl radical, a $C_1$–$C_6$monohydroxyalkyl radical, a $C_2$–$C_6$polyhydroxyalkyl radical, a cyano($C_1$–$C_6$) alkyl radical, a tri($C_1$–$C_6$)alkylsilane($C_1$–$C_6$)alkyl radical, a ($C_1$–$C_6$)alkoxy($C_1$–$C_6$)alkyl radical, a carbamyl($C_1$–$C_6$)alkyl radical, a ($C_1$–$C_6$) alkylcarboxy($C_1$–$C_6$)alkyl radical, a benzyl radical or a second group Z which is identical to or different from the first group Z;

$R_6$, $R_7$ and $R_8$, which may be identical or different, represent a $C_1$–$C_6$alkyl radical, a $C_1$–$C_6$monohydroxyalkyl radical, a $C_2$–$C_6$polyhydroxyalkyl radical, a ($C_1$–$C_6$)alkoxy ($C_1$–$C_6$)alkyl radical, a cyano($C_1$–$C_6$)alkyl radical, an aryl radical, a benzyl radical, a $C_1$–$C_6$amidoalkyl radical, a tri($C_1$–$C_6$)alkylsilane($C_1$–$C_6$)alkyl radical or a $C_1$–$C_6$aminoalkyl radical in which the amine is protected with a ($C_1$–$C_6$)alkylcarbonyl, carbamyl or $C_1$–$C_6$alkylsulphonyl radical; two of the radicals $R_6$, $R_7$ and $R_8$ can together also form, with the nitrogen atom to which they are attached, a saturated 5- or 6-membered carbon-based ring or a ring containing one or more hetero atoms such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$alkyl radical, a $C_1$–$C_6$monohydroxyalkyl radical, a $C_2$–$C_6$polyhydroxyalkyl radical, a nitro radical, a cyano radical, a cyano($C_1$–$C_6$)alkyl radical, a $C_1$–$C_6$alkoxy radical, a tri($C_1$–$C_6$)alkylsilane ($C_1$–$C_6$)alkyl radical, an amido radical, an aldehydo radical, a carboxyl radical, a keto($C_1$–$C_6$)alkyl radical, a thio radical, a $C_1$–$C_6$thioalkyl radical, a $C_1$–$C_6$alkylthio radical, an amino radical or an amino radical protected with a ($C_1$–$C_6$)alkylcarbonyl, carbamyl or $C_1$–$C_6$alkylsulphonyl radical; one of the radicals $R_6$, $R_7$ and $R_8$ can also represent a second group Z which is identical to or different from the first group Z;

$R_9$ represents a $C_1$–$C_6$alkyl radical; a $C_1$–$C_6$monohydroxyalkyl radical; a $C_2$–$C_6$polyhydroxyalkyl radical; an aryl radical; a benzyl radical; a $C_1$–$C_6$aminoalkyl radical, a $C_1$–$C_6$aminoalkyl radical in which the amine is protected with a ($C_1$–$C_6$)alkylcarbonyl, carbamyl or $C_1$–$C_6$alkylsulphonyl radical; a carboxy ($C_1$–$C_6$)

alkyl radical; a cyano($C_1$–$C_6$)alkyl radical; a carbamyl($C_1$–$C_6$)alkyl radical; a $C_1$–$C_6$trifluoroalkyl radical; a tri($C_1$–$C_6$)alkylsilane($C_1$–$C_6$)alkyl radical; a $C_1$–$C_6$sulphonamidoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N—($C_1$–$C_6$) alkylcarbamyl($C_1$–$C_6$)alkyl radical; an N—($C_1$–$C_6$) alkylsulphonamido($C_1$–$C_6$) alkyl radical;

a and y are integers equal to 0 or 1; with the following conditions:
  in the unsaturated cationic groups of formula (II):
    when a=0, the linker arm D is attached to the nitrogen atom,
    when a=1, the linker arm D is attached to one of the ring members E, G, J or L,
    y can take the value 1 only:
      1) when the ring members E, G, J and L simultaneously represent a carbon atom and when the radical $R_5$ is borne by the nitrogen atom of the unsaturated ring; or alternatively
      2) when at least one of the ring members E, G, J and L represents a nitrogen atom to which the radical $R_5$ is attached;
  in the unsaturated cationic groups of formula
    when a=0, the linker arm D is attached to the nitrogen atom,
    when a=1, the linker arm D is attached to one of the ring members E, G, J, L or M,
    y can take the value 1 only when at least one of the ring members E, G, J, L and M represents a divalent atom and when the radical $R_5$ is borne by the nitrogen atom of the unsaturated ring;
  in the cationic groups of formula (IV):
    when a=0, then the linker arm D is attached to the nitrogen atom bearing the radicals $R_6$ to $R_8$,
    when a=1, then two of the radicals $R_6$ to $R_8$ form, together with the nitrogen atom to which they are attached, a saturated 5- or 6-membered ring as defined above, and the linker arm D is borne by a carbon atom of the said saturated ring;
  $X^-$ represents a monovalent or divalent anion and is preferably chosen from a halogen atom such as chlorine, bromine, fluorine or iodine, a hydroxide, a hydrogen sulphate or a $C_1$–$C_6$alkyl sulphate such as, for example, a methyl sulphate or an ethyl sulphate; it being understood that:
    the number of cationic groups Z is at least equal to 1.

As mentioned above, the colorations obtained with the oxidation dye composition containing the dye(s) of formula (I) in accordance with the invention are strong and produce a wide range of shades and colours. They moreover have excellent properties of resistance to the action of various external agents (light, bad weather, washing, permanent-waving, perspiration and friction). These properties are particularly noteworthy, in particular as regards the resistance of the colorations obtained to the action of light, washing, permanent-waving and perspiration.

In formulae (I), (II), (III) and (IV) above, the alkyl and alkoxy radicals can be linear or branched.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

Among the compounds of formula (I) above which may be mentioned most particularly are:
  4-{3-[(3-hydroxynaphthalene-2-carbonyl)amino] propyl}-4-methylmorpholin-4-ium iodide;
  4-{3-[(3-hydroxynaphthalene-2-carbonyl)amino] propyl}-4-methylmorpholin-4-ium methosulphate;
and the addition salts thereof, with an acid.

The compound(s) of formula (I) in accordance with the invention and/or the addition salts thereof with an acid preferably represent(s) from 0.0005% to 12% by weight approximately relative to the total weight of the dye composition, and even more preferably from 0.005% to 6% by weight approximately relative to this weight.

The nature of the oxidation base(s) which may be used in the dye composition in accordance with the invention is not critical. They are preferably chosen from the oxidation bases conventionally used in oxidation dyeing and among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis (0-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

Among the pyridine derivatives which may be mentioned more particularly are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives which may be mentioned more particularly are the compounds described, for example, in German patent DE 2 359 399 or Japanese patents JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, and the addition salts thereof and the tautomeric forms thereof, when a tautomeric equilibrium exists, and the addition salts thereof with an acid.

Among the pyrazole derivatives which may be mentioned more particularly are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

According to the invention, the dye compositions containing one or more para-phenylenediamines and/or one or more heterocyclic oxidation bases are particularly preferred.

The oxidation base(s) preferably represent(s) from 0.0005% to 12% by weight approximately relative to the total weight of the dye composition, and even more preferably from 0.005% to 6% by weight approximately relative to this weight.

In addition to the compound(s) of formula (I) above, the dye composition in accordance with the invention can also include one or more additional couplers which can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these additional couplers preferably represent from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The medium which is suitable for dyeing (or the support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1% and 40% by weight approximately relative to the total weight of the dye composition, and even more preferably between 5% and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

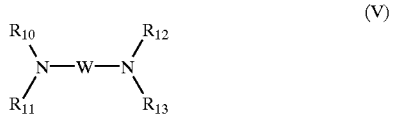

in which W is a propylene residue which is unsubstituted or substituted with a hydroxyl group or a $C_1$–$C_6$alkyl radical; $R_{10}$, $R_{11}$, $R_{12}$ and $R_{13}$, which may be identical or different, represent a hydrogen atom, a $C_1$–$C_6$alkyl radical or a $C_1$–$C_6$hydroxyalkyl radical.

The oxidation dye compositions in accordance with the invention can also include at least one direct dye, in particular in order to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for the oxidation dyeing of keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition applied simultaneously or sequentially.

According to one preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates and persalts such as perborates and persulphates, and enzymes such as peroxidases, laccases, tyrosinases and oxidoreductases among which mention may be made in particular of pyranose oxidases, glucose oxidases, glycerol oxidases, lactate oxidases, pyruvate oxidases and uricases.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR-2 586 913 in the name of the Applicant.

Certain compounds of formula (I) are novel per se and in this respect constitute another subject of the invention. These novel compounds, as well as the addition salts thereof with an acid, correspond to formula (I') below:

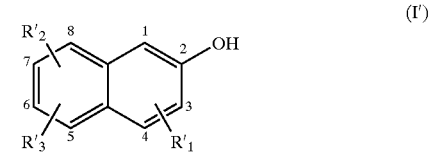

in which $R'_1$, $R'_2$ and $R'_3$ can take the same meanings as those indicated above for $R_1$, $R_2$ and $R_3$; it being understood that when two of the radicals $R'_1$ to $R'_3$ simultaneously represent a hydrogen atom, and when the other radical $R'_1$ to $R'_3$ represents a radical containing an amido or carboxyl function, then the said amido or carboxyl function is not directly attached to the naphthol ring system; and with the exclusion of:

6-hydroxy-N,N,N-trimethyl-1-naphthalenemethanaminium chloride; and

[(2-hydroxy-1-naphthyl)methyl]trimethylammonium iodide.

The addition salts with an acid of the compounds of formula (I') can be chosen from the hydrochlorides, hydrobromides, sulphates, citrates, succinates, tartrates, lactates and acetates.

The compounds of formula (I') in accordance with the invention can readily be obtained according to methods that are well known in the prior art for producing quaternized amines, for example:

in one step, by condensation of a compound comprising a haloalkyl radical with a compound bearing a tertiary amine radical, or by condensation of a compound bearing a tertiary amine radical with a compound bearing a haloalkyl radical;

or in two steps, by condensation of a compound bearing a haloalkyl radical with a compound bearing a secondary amine, or by condensation of an acid chloride with an alkylamine which is disubstituted on the amino group, followed by quaternization with an alkylating agent.

When the synthesis is complete, the compounds of formula (I') in accordance with the invention can, if necessary, be recovered by methods that are well known in the prior art, such as crystallization or distillation.

Finally, a subject of the invention is the use of the compounds of formula (I') as couplers for the oxidation dyeing of keratin fibres, and in particular of human keratin fibres such as the hair.

The examples which follow are intended to illustrate the invention without thereby limiting its scope.

PREPARATION EXAMPLES

Preparation Example 1

Synthesis of 4-{3-[(3-Hydroxynaphthalene-2-carbonyl)amino]propyl}-4-methylmorpholin-4-ium Iodide

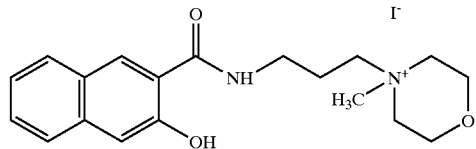

6.2 g of methyl iodide were added dropwise at 80° C. to a solution of 12.6 g of 3-hydroxynaphthalene-2-carboxylic acid (3-morpholin-4-ylpropyl)amide (RN 10155-47-2) in 60 ml of chlorobenzene. After refluxing for 4 hours, the suspension was cooled, filtered on a sinter funnel and spin-filtered. The white precipitate was washed with 20 ml of chlorobenzene and then with 20 ml of petroleum ether. The precipitate was then dried under vacuum. 12.5 g of a white solid of 4-{3-[(3-hydroxynaphthalene-2-carbonyl)amino]propyl}-4-methylmorpholin-4-ium iodide were obtained in a yield of 69%, melting at a temperature above 260° C. (Kofler) and the elemental analysis of which, calculated for $C_{19}H_{25}N_2O_3.I$, was:

| % | C | H | N | O | I |
|---|---|---|---|---|---|
| Calculated | 50.01 | 5.52 | 6.14 | 10.52 | 27.81 |
| Found | 49.08 | 5.71 | 5.93 | 11.07 | 28.21 |

Preparation Example 2

Synthesis of 4-{3-[(3-Hydroxynaphthalene-2-carbonyl)amino]propyl}-4-methylmorpholin-4-ium Methosulphate

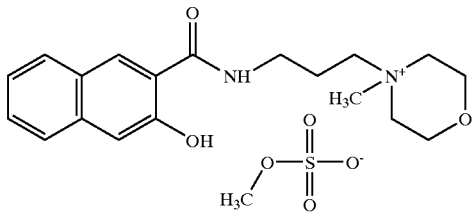

5.6 g of methyl iodide were added dropwise at 60° C. to a solution of 12.6 g of 3-hydroxynaphthalene-2-carboxylic acid (3-morpholin-4-ylpropyl)amide (RN 10155-47-2) in 60 ml of chlorobenzene. After 45 minutes at 60° C., the suspension was cooled and then separated by settling. The white solid obtained was ground, reslurried in petroleum ether, filtered off on a sinter funnel, spin-filtered and then washed with 20 ml of chlorobenzene and then with 20 ml of petroleum ether. The precipitate was dried under vacuum.

16.6 g of a white solid of 4-{3-[(3-hydroxynaphthalene-2-carbonyl)amino]propyl}-4-methylmorpholin-4-ium methosulphate were obtained in a yield of 94.4%, melting at a temperature above 260° C. (Kofler) and the elemental analysis of which, calculated for $C_{19}H_{25}N_2O_3.CH_3O_4S$, was:

| % | C | H | N | O | S |
|---|---|---|---|---|---|
| Calculated | 54.53 | 6.41 | 6.36 | 25.42 | 7.28 |
| Found | 53.78 | 6.59 | 5.95 | 25.64 | 8.04 |

DYEING EXAMPLES

Examples 1 to 4 of Dyeing in an Alkaline Medium

The dye compositions below were prepared (contents in grams):

| EXAMPLE | 1 | 2 | 3 | 4 |
|---|---|---|---|---|
| 4-{3-[(3-Hydroxynaphthalene-2-carbonyl)amino]propyl}-4-methylmorpholin-4-ium iodide (compound of formula (I)) | 1.37 | 1.37 | 1.37 | 1.37 |
| para-Phenylenediamine dihydrochloride (oxidation base) | 0.540 | — | — | — |
| para-Tolylenediamine dihydrochloride (oxidation base) | — | 0.585 | — | — |
| Pyrazolo[1,5-a]pyrimidine-3,7-diamine dihydrochloride (oxidation base) | — | — | 0.666 | — |
| N,N-Bis(hydroxyethyl)-para-phenylenediamine dihydrochloride (coupler) | — | — | — | 0.807 |
| Common dye support No. 1 | (*) | (*) | (*) | (*) |
| Demineralized water qs | 100 g | 100 g | 100 g | 100 g |

(*) Common dye support No. 1:

| | |
|---|---|
| Benzyl alcohol | 2.0 g |
| Polyethylene glycol containing 6 mol of ethylene oxide | 3.0 g |
| 96° ethanol | 20.0 g |
| (C$_8$-C$_{10}$)Alkylpolyglucoside as an aqueous solution containing 60% active material (A.M.), buffered with ammonium citrate, sold under the name Oramix CG 110 ® by the company SEPPIC | 6.0 g |
| Aqueous ammonia containing 20% NH$_3$ | 10.0 g |
| Sodium metabisulfite containing 35% active material | 0.228 g |
| Pentasodium salt of diethylenetriamine-pentaacetic acid | 1.1 g |

At the time of use, each of the above dye compositions was mixed weight for weight with a 20-volumes hydrogen peroxide solution of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Golden brown |
| 2 | 10 ± 0.2 | Light golden |
| 3 | 10 ± 0.2 | Rosewood |
| 4 | 10 ± 0.2 | Pale golden-green |

What is claimed is:

1. A composition for oxidation dyeing keratin fibres comprising, in a medium appropriate for dyeing:

at least one coloring compound chosen from oxidation bases and acid addition salts of said oxidation bases, and at least one coupler chosen from compounds of formula (I) below and acid addition salts thereof:

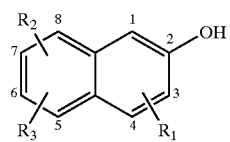

(I)

wherein:

groups R$_1$, R$_2$ and R$_3$, which may be identical or different, are each chosen from:
(1) a hydrogen and a halogen atom;
(2) groups Z chosen from groups of formulae (II), (III), and (IV):

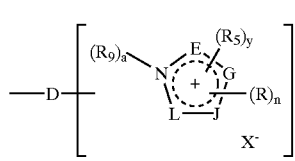

(II)

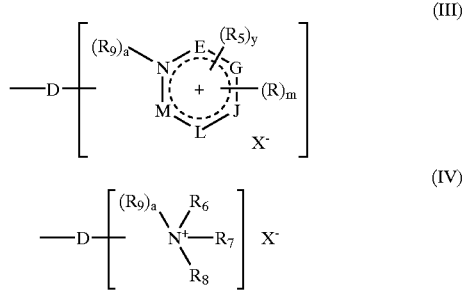

wherein:

linker D is chosen from linear and branched divalent alkylene groups, optionally comprising at least one hetero atom, and optionally substituted with at least one group chosen from hydroxyl groups and C$_1$-C$_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;

m is an integer ranging from 0 to 5;

R, which may be identical or different, are each chosen from:
  groups Z, as defined above;
  a halogen atom, a hydroxyl group, C$_1$-C$_6$alkyl groups, C$_1$-C$_6$monohydroxyalkyl groups, C$_2$-C$_6$polyhydroxyalkyl groups, nitro groups, cyano groups, cyano(C$_1$-C$_6$)alkyl groups, C$_1$-C$_6$alkoxy groups, tri(C$_1$-C$_6$)alkylsilane (C$_1$-C$_6$)alkyl groups, amido groups, aldehydo groups, carboxyl groups, (C$_1$-C$_6$) alkylcarbonyl groups, thio groups, C$_1$-C$_6$thioalkyl groups, C$_1$-C$_6$alkylthio groups, amino groups optionally protected with at least one group chosen from (C$_1$-C$_6$) alkylcarbonyl groups, carbamyl groups and C$_1$-C$_6$alkylsulfonyl groups, groups NHR$^2$ and NR$^2$R''' in which R$^2$ and R''', which may be identical or different, are each chosen from C$_1$-C$_6$alkyl groups, C$_1$-C$_6$monohydroxyalkyl groups and C$_2$-C$_6$polyhydroxyalkyl groups;

R$_5$ is chosen from C$_1$-C$_6$alkyl groups, C$_1$-C$_6$monohydroxyalkyl groups, C$_2$-C$_6$polyhydroxyalkyl groups, cyano(C$_1$-C$_6$) alkyl groups, tri(C$_1$-C$_6$)alkylsilane(C$_1$-C$_6$)alkyl groups, (C$_1$-C$_6$)alkoxy(C$_1$-C$_6$)alkyl groups, carbamyl(C$_1$-C$_6$)alkyl groups, (C$_1$-C$_6$) alkylcarboxy(C$_1$-C$_6$)alkyl groups, benzyl groups, and groups Z, as defined above;

R$_6$, R$_7$ and R$_8$, which may be identical or different, are each chosen from:
  C$_1$-C$_6$alkyl groups, C$_1$-C$_6$monohydroxyalkyl groups, C$_2$-C$_6$polyhydroxyalkyl groups, (C$_1$-C$_6$)alkoxy(C$_1$-C$_6$)alkyl groups, cyano (C$_1$-C$_6$)alkyl groups, aryl groups, benzyl groups, C$_1$-C$_6$amidoalkyl groups, tri(C$_1$-C$_6$) alkylsilane(C$_1$-C$_6$)alkyl groups, C$_1$-C$_6$aminoalkyl groups, wherein the amine is protected with at least one group chosen from (C$_1$-C$_6$)alkylcarbonyl groups, carbamyl groups and C$_1$-C$_6$alkylsulfonyl groups;
  two of the groups R$_6$, R$_7$ and R$_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:
$C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:
in said groups of formula (II) at least one of the following applies:
1) a=0, y=0, and said linker D is bonded to the nitrogen atom that is bonded to E and L;
2) a=0, y=1, E, G, J, and L are carbon atoms, and said linker D and $R_5$ are bonded to the nitrogen atom that is bonded to E and L;
3) a=0, y=1, at least one of said ring members E, G, J, and L is a nitrogen atom to which $R_5$ is bonded, and said linker D is bonded to the nitrogen atom that is bonded to E and L:
4) a=1, y=0, said linker D is bonded to one of said ring members chosen from E, G, J and L;
5) a=1, y=1, said ring members E, G, J, and L are carbon atoms one of which is bonded to said linker D, and $R_5$ is bonded to the nitrogen atom that is bonded to E and L; and
6) a=1, y=1, said linker D is bonded to one of said ring members chosen from E, G, J and L, and at least one of said ring members E, G, J, and L is a nitrogen atom to which $R_5$ is bonded;

in said groups of formula (III) at least one of the following applies:
1) a=0, y=0, said linker D is bonded to the nitrogen atom that is bonded to E and M;
2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:
1) a=0, y=0 or 1, said linker D is bonded to the nitrogen that is bonded to groups $R_6$, $R_7$, and $R_8$;
2) a=1, y=0 or 1, two of the groups $R_6$, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

X_ is chosen from monovalent anions and divalent anions;

provided that said compounds of formula (I) comprise at least one group Z;

(3) ($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino ($C_1$–$C_6$)alkylcarbonyl groups, N,N-di($C_1$–$C_6$) alkylamino($C_1$–$C_6$)alkylcarbonyl groups, amino ($C_1$–$C_6$)alkylcarbonyl($C_1$–$C_6$)alkyl groups, N—Z-amino($C_1$–$C_6$)alkylcarbonyl($C_1$–$C_6$)alkyl groups, N—($C_1$–$C_6$)alkylamino($C_1$–$C_6$)alkylcarbonyl ($C_1$–$C_6$)alkyl groups, N,N-di($C_1$–$C_6$)alkylamino ($C_1$–$C_6$)alkylcarbonyl($C_1$–$C_6$)alkyl groups, carboxyl groups, ($C_1$–$C_6$)alkylcarboxyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$) alkylaminosulfonyl groups, $C_1$–$C_6$aminosulfonylalkyl groups, $C_1$–$C_6$N—Z-aminosulfonylalkyl groups, N—($C_1$–$C_6$) alkylaminosulfonyl($C_1$–$C_6$)alkyl groups, N,N-di ($C_1$–$C_6$)alkylaminosulfonyl($C_1$–$C_6$)alkyl groups, carbamyl groups, N—($C_1$–$C_6$)alkylcarbamyl groups, N,N-di($C_1$–$C_6$)alkylcarbamyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, $C_1$–$C_6$alkyl groups, $C_1$–$C_6$monohydroxyalkyl groups, $C_2$–$C_6$polyhydroxyalkyl groups, ($C_1$–$C_6$)alkoxy ($C_1$–$C_6$)alkyl groups, $C_1$–$C_6$trifluoroalkyl groups, and cyano groups, wherein Z is defined above;

(4) groups —$OR_4$ and groups —$SR_4$, wherein said $R_4$ are chosen from:
$C_1$–$C_6$alkyl groups, $C_1$–$C_6$monohydroxyalkyl groups, and $C_2$–$C_6$polyhydroxyalkyl groups, groups Z as defined above, ($C_1$–$C_6$)alkoxy ($C_1$–$C_6$)alkyl groups, aryl groups, benzyl groups, carboxy($C_1$–$C_6$)alkyl groups, ($C_1$–$C_6$) alkylcarboxy($C_1$–$C_6$)alkyl groups, cyano($C_1$–$C_6$) alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$trifluoroalkyl groups, $C_1$–$C_6$aminosulfonylalkyl groups, $C_1$–$C_6$N—Z-aminosulfonylalkyl groups, N—($C_1$–$C_6$)

alkylaminosulfonyl($C_1$–$C_6$)alkyl groups, N,N-di($C_1$–$C_6$)alkylaminosulfonyl($C_1$–$C_6$)alkyl groups, ($C_1$–$C_6$)alkylsulfinyl($C_1$–$C_6$)alkyl groups, ($C_1$–$C_6$)alkylsulfonyl($C_1$–$C_6$)alkyl groups, ($C_1$–$C_6$)alkylcarbonyl($C_1$–$C_6$)alkyl groups, $C_1$–$C_6$aminoalkyl groups, wherein the alkyl is optionally substituted with at least one hydroxyl group, $C_1$–$C_6$aminoalkyl groups, wherein said alkyl is unsubstituted or substituted with at least one hydroxyl group and, wherein said amine is substituted with one or two groups, which may be identical or different, each chosen from $C_1$–$C_6$alkyl groups, $C_1$–$C_6$monohydroxyalkyl groups, $C_2$–$C_6$polyhydroxyalkyl groups, ($C_1$–$C_6$) alkylcarbonyl groups, formyl groups, trifluoro ($C_1$–$C_6$)alkylcarbonyl groups, ($C_1$–$C_6$) alkylcarboxyl groups, carbamyl groups, N—($C_1$–$C_6$)alkylcarbamyl groups, N,N-di($C_1$–$C_6$)alkylcarbamyl groups, thiocarbamyl groups and $C_1$–$C_6$alkylsulfonyl groups and groups Z as defined above, and, when said amine is substituted with two groups, said two groups may optionally form, together with the nitrogen atom to which said two groups are commonly bonded, at least one ring chosen from 5- and 6-membered carbon-based rings and rings comprising at least one hetero atom;
(5) amino groups protected with at least one group chosen from
($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$) alkylamino($C_1$–$C_6$)alkylcarbonyl groups, N,N-di($C_1$–$C_6$)alkylamino($C_1$–$C_6$)alkylcarbonyl groups, ($C_1$–$C_6$)alkylcarboxyl groups, carbamyl groups, N—($C_1$–$C_6$)alkylcarbamyl groups, N,N-di ($C_1$–$C_6$)alkylcarbamyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$) alkylaminosulfonyl groups, thiocarbamyl groups, formyl groups, and groups Z as defined above wherein said linker D in said groups Z comprises at least one ketone functional group directly bonded to the nitrogen atom of said amino group;
(6) $C_1$–$C_6$aminoalkyl groups, wherein the alkyl is optionally substituted with at least one hydroxyl group;
(7) amino($C_1$–$C_6$)alkyl groups, wherein the alkyl is optionally substituted with at least one hydroxyl group and wherein said amino is substituted with one or two groups, which may be identical or different, chosen from alkyl groups, $C_1$–$C_6$monohydroxyalkyl groups, $C_2$–$C_6$polyhydroxyalkyl groups, ($C_1$–$C_6$) alkylcarbonyl groups, carbamyl groups, N—($C_1$–$C_6$) alkylcarbamyl groups, N,N-di($C_1$–$C_6$)alkylcarbamyl groups, ($C_1$–$C_6$)alkylsulfonyl groups, formyl groups, trifluoro($C_1$–$C_6$)alkylcarbonyl groups, ($C_1$–$C_6$) alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom.

2. A composition according to claim 1, wherein said linker D comprises from 1 to 14 carbon atoms.

3. A composition according to claim 1, wherein said linker D optionally comprises at least one hetero atom chosen from oxygen, sulfur and nitrogen atoms.

4. A composition according to claim 1, wherein said $X^-$ is chosen from halogen anions, hydroxide anions, hydrogen sulfate anions, and $C_1$–$C_6$alkyl sulfate anions.

5. A composition according to claim 4, wherein said halogen anions are chosen from chloride, bromide, fluoride and iodide.

6. A composition according to claim 4, wherein said $C_1$–$C_6$alkyl sulfate anions are chosen from methyl sulfate anions and ethyl sulfate anions.

7. A composition according to claim 1, wherein said groups Z of formula (II) are rings chosen from pyrrole, imidazole, pyrazole, oxazole, thiazole and triazole rings.

8. A composition according to claim 1, wherein said compounds of formula (I) comprise at least one group of formula (II) chosen from pyrrole rings, imidazole rings, pyrazole rings, oxazole rings, thiazole rings and triazole rings.

9. A composition according to claim 1 wherein said groups Z of formula (III) are rings chosen from pyridine, pyrimidine, pyrazine, oxazine and triazine rings.

10. A composition according to claim 1, wherein said compounds of formula (I) comprise at least one group of formula (III) chosen from pyridine rings, pyrimidine rings, pyrazine rings, oxazine rings and triazine rings.

11. A composition according to claim 1, wherein two of said groups $R_6$, $R_7$ and $R_8$ form, together with the nitrogen cation to which said groups are commonly bonded, at least one ring chosen from pyrrolidine, piperidine, piperazine and morpholine rings.

12. A composition according to claim 1, wherein said at least one coupler is chosen from:
4-{3-[(3-hydroxynaphthalene-2-carbonyl)amino]-propyl}-4-methylmorpholin-4-ium iodide;
4-{3-[(3-hyroxy-naphthalene-2-carbonyl)amino]-propyl}-4-methylmorholin-4-ium methosulphate and acid addition salts thereof.

13. A composition according to claim 1, wherein said at least one coupler is present in an amount ranging from 0.0005% to 12% by weight relative to the total weight of the dye composition.

14. A composition according to claim 13, wherein said at least one coupler is present in an amount ranging from 0.005% to 6% by weight, relative to the total weight of the dye composition.

15. A composition according to claim 1, wherein said at least one coloring compound is chosen from oxidation bases chosen from para-phenylenediamines, bis(phenyl)alkylenediamines, para-aminophenols, ortho-aminophenols, heterocyclic bases, and acid addition salts of said oxidation bases.

16. A composition according to claim 15, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethylpara-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and acid addition salts thereof.

17. A composition according to claim 15, wherein said para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and acid addition salts thereof.

18. A composition according to claim 15, wherein said bis(phenyl)alkylenediamines are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylene diamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylene diamine and 1,8-bis(2,5-diaminophenoxy)-3,5-dioxaoctane, and acid addition salts thereof.

19. A composition according to claim 15, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and acid addition salts thereof.

20. A composition according to claim 15, wherein said ortho-aminophenols are chosen from 2-aminophenol, 2-amino-5-methylphenol, 2-amino-6-methylphenol and 5-acetamido-2-aminophenol, and acid addition salts thereof.

21. A composition according to claim 15, wherein said heterocyclic bases are chosen from pyridine derivatives, pyrimidine derivatives, pyrazole derivatives, and acid addition salts thereof.

22. A composition according to claim 21, wherein said pyridine derivatives are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and acid addition salts thereof.

23. A composition according to claim 21, wherein said pyrimidine derivatives are chosen from 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives, and acid addition salts thereof.

24. A composition according to claim 23, wherein said pyrazolopyrimidine derivatives are chosen from pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, and acid addition salts thereof, the tautomeric forms of the foregoing, when a tautomeric equilibrium exists, and and acid addition salts thereof.

25. A composition according to claim 21, wherein said pyrazole derivatives are chosen from 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-3-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and acid addition salts thereof.

26. A composition according to claim 1, wherein said at least one coloring compound is chosen from para-phenylenediamines and heterocyclic oxidation bases.

27. A composition according to claim 26, wherein said at least one coloring compound is chosen from para-phenylenediamines.

28. A composition according to claim 26, wherein said at least one coloring compound is chosen from heterocyclic oxidation bases.

29. A composition according to claim 1, wherein said at least one coloring compound is present in an amount ranging from 0.0005% to 12% by weight relative to the total weight of the dye composition.

30. A composition according to claim 1, wherein said composition for dyeing keratin fibers further comprises at least one additional coupler.

31. A composition according to claim 30, wherein said at least one additional coupler is chosen from meta-phenylenediamines, meta-aminophenols, meta-diphenols, heterocyclic couplers, direct dyes and acid addition salts thereof.

32. A composition according to claim 31, wherein said heterocyclic couplers are chosen from indole derivatives, indolene derivatives, pyridine derivatives and pyrazolones, and acid addition salts thereof.

33. A composition according to claim 31, wherein said heterocyclic couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6- dihydroxy-4-methylpyridine, 1H-3-methylpyrazol-5-one and 1-phenyl-3-methylpyrazol-5-one, and acid addition salts thereof.

34. A composition according to claim 30, wherein said at least one additional coupler is present in an amount ranging from 0.0001 % to 10% by weight relative to the total weight of the dye composition.

35. A composition according to claim 34, wherein said at least one additional coupler is present in an amount ranging from 0.005% to 5% by weight relative to the total weight of the dye composition.

36. A composition according to claim 1, wherein said acid addition salts are chosen from hydrochlorides, hydrobromides, sulfates, citrates, succinates, tartrates, lactates and acetates.

37. A composition according to claim 15, wherein said acid addition salts are chosen from hydrochlorides, hydrobromides, sulfates, citrates, succinates, tartrates, lactates and acetates.

38. A composition according to claim 31, wherein said acid addition salts are chosen from hydrochlorides, hydrobromides, sulfates, citrates, succinates, tartrates, lactates and acetates.

39. A composition according to claim 1, wherein said medium appropriate for dyeing is a media chosen from media comprising water and media comprising water and at least one organic solvent.

40. A composition according to claim 39, wherein said at least one organic solvent is chosen from $C_1$–$C_4$alkanols, glycerol, glycols, glycol ethers, and aromatic alcohols.

41. A composition according to claim 40, wherein said $C_1$–$C_4$alkanols are chosen from ethanol and isopropanol.

42. A composition according to claim 40, wherein said glycol ethers are chosen from 2-butoxyethanol, propylene glycol, propylene glycol monomethyl ether, diethylene glycol monoethyl ether and monomethyl ether.

43. A composition according to claim 40, wherein said aromatic alcohols are chosen from benzyl alcohol and phenoxyethanol.

44. A composition according to claim 39, wherein said at least one organic solvent is present in an amount ranging from 1% to 40% by weight relative to the total weight of the dye composition.

45. A composition according to claim 44, wherein said at least one organic solvent is present in an amount ranging from 5% to 30% by weight relative to the total weight of the dye composition.

46. A composition according to claim 1, wherein said composition for dyeing keratin fibers has a pH ranging from 3 to 12.

47. A composition according to claim 46, wherein said composition for dyeing keratin fibers has a pH ranging from 5 to 11.

48. A composition according to claim 46 further comprising at least one agent for adjusting said pH chosen from acidifying agents and basifying agents.

49. A composition according to claim 48, wherein said acidifying agents are chosen from inorganic acids and organic acids.

50. A composition according to claim 49, wherein said inorganic and organic acids are chosen from hydrochloric acid, orthophosphoric acid, sulfuric acid, carboxylic acids, and sulfonic acids.

51. A composition according to claim 50, wherein said carboxylic acids are chosen from acetic acid, tartaric acid, citric acid and lactic acid.

52. A composition according to claim 48, wherein said basifying agents are chosen from aqueous ammonia, alkaline carbonates, alkanolamines, sodium hydroxide, potassium hydroxide and compounds of formula (V):

$$\begin{array}{c} R_{10} \quad R_{12} \\ \diagdown N-W-N \diagup \\ R_{11} \quad R_{13} \end{array} \quad (V)$$

wherein:

W is a propylene residue chosen from unsubstituted propylene residues and propylene residues substituted with a group chosen from a hydroxyl group and $C_1$–$C_6$alkyl groups;

$R_{10}$, $R_{11}$, $R_{12}$ and $R_{13}$, which may be identical or different, are each units chosen from a hydrogen atom, $C_1$–$C_6$alkyl groups, and $C_1$–$C_6$hydroxyalkyl groups.

53. A composition according to claim 52, wherein said alkanolamines are chosen from mono-, di- and triethanolamine and derivatives thereof.

54. A composition according to claim 1, wherein said composition for dyeing keratin fibers comprises at least one adjuvant.

55. A composition according to claim 54, wherein said at least one adjuvant is chosen from anionic, cationic, nonionic, amphoteric and zwitterionic surfactants, anionic, cationic, nonionic, amphoteric and zwitterionic polymers, inorganic and organic thickeners, antioxidants, penetration agents, sequestering agents, fragrances, buffers, dispersing agents, packaging agents, film-forming agents, ceramides, preserving agents and opacifiers.

56. A composition according to claim 55, wherein said packaging agents are chosen from volatile and nonvolatile, modified and unmodified silicones.

57. A liquid, a cream, or a gel for dyeing keratin fibers comprising, in a medium appropriate for dyeing:
at least one coloring compound chosen from oxidation bases and acid addition salts of said oxidation bases, and
at least one coupler chosen from compounds of formula (I) below and acid addition salts thereof:

$$\begin{array}{c} R_2 \underset{7}{\overset{8}{\diagdown}} \overset{1}{\diagup} \text{OH} \\ \underset{6}{\diagdown} \underset{5}{\diagup} \underset{4}{\diagdown} \\ R_3 \quad R_1 \end{array} \quad (I)$$

wherein:

groups $R_1$, $R_2$ and $R_3$, which may be identical or different, are each chosen from:
(1) a hydrogen and a halogen atom;
(2) groups Z chosen from groups of formulae (II), (III), and (IV):

$$-D - \left[ (R_9)_a \diagdown N \underset{L-J}{\overset{E(R_5)_y}{\diagup}} \underset{+}{G} (R)_n \right] X^- \quad (II)$$

-continued

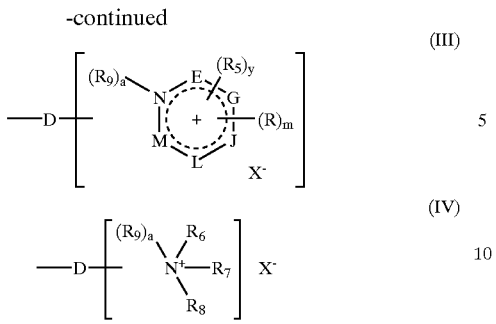

wherein:
linker D is chosen from linear and branched divalent alkylene groups, optionally comprising at least one hetero atom, and optionally substituted with at least one group chosen from hydroxyl groups and $C_1$–$C_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;

m is an integer ranging from 0 to 5;

R, which may be identical or different, are each chosen from:
  groups Z, as defined above;
  a halogen atom, a hydroxyl group, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$)alkylsilane($C_1$–$C_6$)alkyl groups, amido groups, aldehydo groups, carboxyl groups, ($C_1$–$C_6$) alkylcarbonyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups, groups $NHR^2$ and $NR^2R'''$ in which $R^2$ and $R'''$, which may be identical or different, are each chosen from $C_1$–$C_6$alkyl groups, $C_1$–$C_6$monohydroxyalkyl groups and $C_2$–$C_6$polyhydroxyalkyl groups;

$R_5$ is chosen from $C_1$–$C_6$alkyl groups, $C_1$–$C_6$monohydroxyalkyl groups, $C_2$–$C_6$polyhydroxyalkyl groups, cyano($C_1$–$C_6$) alkyl groups, tri($C_1$–$C_6$)alkylsilane($C_1$–$C_6$)alkyl groups, ($C_1$–$C_6$)alkoxy($C_1$–$C_6$)alkyl groups, carbamyl($C_1$–$C_6$)alkyl groups, ($C_1$–$C_6$) alkylcarboxy($C_1$–$C_6$)alkyl groups, benzyl groups, and groups Z, as defined above;

$R_6$, $R_7$ and $R_8$, which may be identical or different, are each chosen from:
  $C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, cyano ($C_1$–$C_6$)alkyl groups, aryl groups, benzyl groups, $C_1$–$C_6$amidoalkyl groups, tri($C_1$–$C_6$) alkylsilane($C_1$–$C_6$)alkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups;
  two of the groups $R_6$, $R_7$ and $R_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:
  $C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:
  in said groups of formula (II) at least one of the following applies:
    1) a=0, y=0, and said linker D is bonded to the nitrogen atom that is bonded to E and L;
    2) a=0, y=1, E, G, J, and L are carbon atoms, and said linker D and $R_5$ are bonded to the nitrogen atom that is bonded to E and L;
    3) a=0, y=1, at least one of said ring members E, G, J, and L is a nitrogen atom to which $R_5$ is bonded, and said inker D s bonded to the nitrogen atom that is bonded to E and L;
    4) a=1, y=0, said linker D is bonded to one of said ring members chosen from E, G, J and L;
    5) a=1, y=1, said ring members E, G, J, and L are carbon atoms one of which is bonded to said linker D, and $R_5$ is bonded to the nitrogen atom that is bonded to E and L; and
    6) a=1, y=1, said linker D is bonded to one of said ring members chosen from E, G, J and L, and at least one of said ring members E, G, J, and L is a nitrogen atom to which $R_5$ is bonded;
  in said groups of formula (III) at least one of the following applies:
    1) a=0, y=0, said linker D is bonded to the nitrogen atom that is bonded to E and M;
    2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:
1) a=0, y=0 or 1, said linker D is bonded to the nitrogen that is bonded to groups $R_6$, $R_7$, and $R_8$;
2) a=1, y=0 or 1, two of the groups $R_6$, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

$X^-$ is chosen from monovalent anions and divalent anions;

provided that said compounds of formula (I) comprise at least one group Z;

(3) $(C_1-C_6)$alkylcarbonyl groups, amino$(C_1-C_6)$alkylcarbonyl groups, N—Z-amino$(C_1-C_6)$alkylcarbonyl groups, N—$(C_1-C_6)$alkylamino$(C_1-C_6)$alkylcarbonyl groups, N,N-di$(C_1-C_6)$alkylamino$(C_1-C_6)$alkylcarbonyl groups, amino$(C_1-C_6)$alkylcarbonyl$(C_1-C_6)$alkyl groups, N—Z-amino$(C_1-C_6)$alkylcarbonyl$(C_1-C_6)$alkyl groups, N—$(C_1-C_6)$alkylamino$(C_1-C_6)$alkylcarbonyl$(C_1-C_6)$alkyl groups, N,N-di$(C_1-C_6)$alkylamino$(C_1-C_6)$alkylcarbonyl$(C_1-C_6)$alkyl groups, carboxyl groups, $(C_1-C_6)$alkylcarboxyl groups, $C_1-C_6$alkylsulfonyl groups, aminosulfonyl groups, N—Z-aminosulfonyl groups, $C_1-C_6$N-alkylaminosulfonyl groups, N,N-di$(C_1-C_6)$alkylaminosulfonyl groups, $C_1-C_6$aminosulfonylalkyl groups, $C_1-C_6$N—Z-aminosulfonylalkyl groups, N—$(C_1-C_6)$alkylaminosulfonyl$(C_1-C_6)$alkyl groups, N,N-di$(C_1-C_6)$alkylaminosulfonyl$(C_1-C_6)$alkyl groups, carbamyl groups, N—$(C_1-C_6)$alkylcarbamyl groups, N,N-di$(C_1-C_6)$alkylcarbamyl groups, carbamyl$(C_1-C_6)$alkyl groups, N—$(C_1-C_6)$alkylcarbamyl$(C_1-C_6)$alkyl groups, N,N-di$(C_1-C_6)$alkylcarbamyl$(C_1-C_6)$alkyl groups, $C_1-C_6$alkyl groups, $C_1-C_6$monohydroxyalkyl groups, $C_2-C_6$polyhydroxyalkyl groups, $(C_1-C_6)$alkoxy$(C_1-C_6)$alkyl groups, $C_1-C_6$trifluoroalkyl groups, and cyano groups, wherein Z is defined above;

(4) groups —$OR_4$ and groups —$SR_4$, wherein said $R_4$ are chosen from:
$C_1-C_6$alkyl groups, $C_1-C_6$monohydroxyalkyl groups, and $C_2-C_6$polyhydroxyalkyl groups, groups Z as defined above, $(C_1-C_6)$alkoxy$(C_1-C_6)$alkyl groups, aryl groups, benzyl groups, carboxy$(C_1-C_6)$alkyl groups, $(C_1-C_6)$alkylcarboxy$(C_1-C_6)$alkyl groups, cyano$(C_1-C_6)$alkyl groups, carbamyl$(C_1-C_6)$alkyl groups, N—$(C_1-C_6)$alkylcarbamyl$(C_1-C_6)$alkyl groups, N,N-di$(C_1-C_6)$alkylcarbamyl$(C_1-C_6)$alkyl groups, $C_1-C_6$trifluoroalkyl groups, $C_1-C_6$aminosulfonylalkyl groups, $C_1-C_6$N—Z-aminosulfonylalkyl groups, N—$(C_1-C_6)$alkylaminosulfonyl$(C_1-C_6)$alkyl groups, N,N-di$(C_1-C_6)$alkylaminosulfonyl$(C_1-C_6)$alkyl groups, $(C_1-C_6)$alkylsulfinyl$(C_1-C_6)$alkyl groups, $(C_1-C_6)$alkylsulfonyl$(C_1-C_6)$alkyl groups, $(C_1-C_6)$alkylcarbonyl$(C_1-C_6)$alkyl groups, $C_1-C_6$aminoalkyl groups, wherein the alkyl is optionally substituted with at least one hydroxyl group, $C_1-C_6$aminoalkyl groups, wherein said alkyl is unsubstituted or substituted with at least one hydroxyl group and, wherein said amine is substituted with one or two groups, which may be identical or different, each chosen from $C_1-C_6$alkyl groups, $C_1-C_6$monohydroxyalkyl groups, $C_2-C_6$polyhydroxyalkyl groups, $(C_1-C_6)$alkylcarbonyl groups, formyl groups, trifluoro$(C_1-C_6)$alkylcarbonyl groups, $(C_1-C_6)$alkylcarboxyl groups, carbamyl groups, N—$(C_1-C_6)$alkylcarbamyl groups, N,N-di$(C_1-C_6)$alkylcarbamyl groups, thiocarbamyl groups and $C_1-C_6$alkylsulfonyl groups and groups Z as defined above, and, when said amine is substituted with two groups, said two groups may optionally form, together with the nitrogen atom to which said two groups are commonly bonded, at least one ring chosen from 5-and 6-membered carbon-based rings and rings comprising at least one hetero atom;

(5) amino groups protected with at least one group chosen from
$(C_1-C_6)$alkylcarbonyl groups, $(C_1-C_6)$alkylcarboxyl groups, trifluoro$(C_1-C_6)$alkylcarbonyl groups, amino$(C_1-C_6)$alkylcarbonyl groups, N—Z-amino$(C_1-C_6)$alkylcarbonyl groups, N—$(C_1-C_6)$alkylamino$(C_1-C_6)$alkylcarbonyl groups, N,N-di$(C_1-C_6)$alkylamino$(C_1-C_6)$alkylcarbonyl groups, $(C_1-C_6)$alkylcarboxyl groups, carbamyl groups, N—$(C_1-C_6)$alkylcarbamyl groups, N,N-di$(C_1-C_6)$alkylcarbamyl groups, $C_1-C_6$alkylsulfonyl groups, aminosulfonyl groups, N—Z-aminosulfonyl groups, $C_1-C_6$N-alkylaminosulfonyl groups, N,N-di$(C_1-C_6)$alkylaminosulfonyl groups, thiocarbamyl groups, formyl groups, and groups Z as defined above wherein said linker D in said groups Z comprises at least one ketone functional group directly bonded to the nitrogen atom of said amino group;

(6) $C_1-C_6$aminoalkyl groups, wherein the alkyl is optionally substituted with at least one hydroxyl group;

(7) amino$(C_1-C_6)$alkyl groups, wherein the alkyl is optionally substituted with at least one hydroxyl group and wherein said amino is substituted with one or two groups, which may be identical or different, chosen from alkyl groups, $C_1-C_6$monohydroxyalkyl groups, $C_2-C_6$polyhydroxyalkyl groups, $(C_1-C_6)$alkylcarbonyl groups, carbamyl groups, N—$(C_1-C_6)$alkylcarbamyl groups, N,N-di$(C_1-C_6)$alkylcarbamyl groups, $(C_1-C_6)$alkylsulfonyl groups, formyl groups, trifluoro$(C_1-C_6)$alkylcarbonyl groups, $(C_1-C_6)$alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom.

58. A composition according to claim 57, wherein said keratin fibers are human hair.

59. A process for oxidation dyeing keratin fibers comprising (A) applying to said keratin fibers at least one dyeing composition comprising, in a medium appropriate for dyeing:

at least one coloring compound chosen from oxidation bases and acid addition salts of said oxidation bases, and at least one coupler chosen from compounds of formula (I) below and acid addition salts thereof:

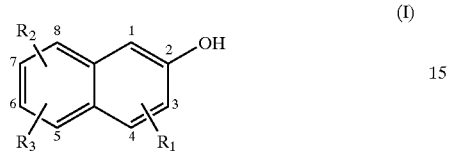

(I)

wherein:
groups $R_1$, $R_2$ and $R_3$, which may be identical or different, are each chosen from:
(1) a hydrogen and a halogen atom;
(2) groups Z chosen from groups of formulae (II), (III), and (IV):

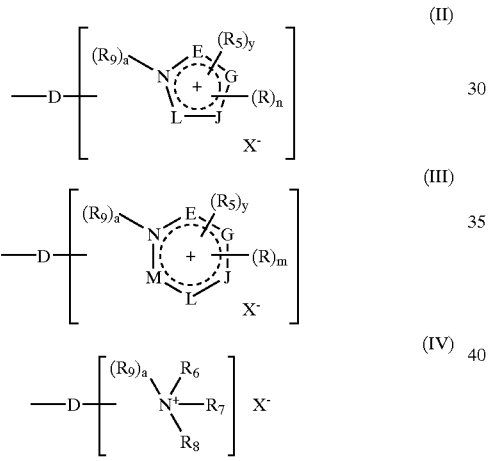

wherein:
linker D is chosen from linear and branched divalent alkylene groups, optionally comprising at least one hetero atom, and optionally substituted with at least one group chosen from hydroxyl groups and $C_1$–$C_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;
m is an integer ranging from 0 to 5;
R, which may be identical or different, are each chosen from:
  groups Z, as defined above;
  a halogen atom, a hydroxyl group, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$)alkylsilane ($C_1$–$C_6$)alkyl groups, amido groups, aldehydo groups, carboxyl groups, ($C_1$–$C_6$) alkylcarbonyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups, groups $NHR^2$ and $NR^2R'''$ in which $R^2$ and $R'''$, which may be identical or different, are each chosen from $C_1$–$C_6$alkyl groups, $C_1$–$C_6$monohydroxyalkyl groups and $C_2$–$C_6$polyhydroxyalkyl groups;

$R_5$ is chosen from $C_1$–$C_6$alkyl groups, $C_1$–$C_6$monohydroxyalkyl groups, $C_2$–$C_6$polyhydroxyalkyl groups, cyano($C_1$–$C_6$) alkyl groups, tri($C_1$–$C_6$)alkylsilane($C_1$–$C_6$)alkyl groups, ($C_1$–$C_6$)alkoxy($C_1$–$C_6$)alkyl groups, carbamyl($C_1$–$C_6$)alkyl groups, ($C_1$–$C_6$) alkylcarboxy($C_1$–$C_6$)alkyl groups, benzyl groups, and groups Z, as defined above;

$R_6$, $R_7$ and $R_8$, which may be identical or different, are each chosen from:
  $C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, cyano ($C_1$–$C_6$)alkyl groups, aryl groups, benzyl groups, $C_1$–$C_6$amidoalkyl groups, tri($C_1$–$C_6$) alkylsilane($C_1$–$C_6$)alkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups;

two of the groups $R_6$, $R_7$ and $R_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:
  $C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$)

alkylketo($C_1$–$C_6$)alkyl groups, N—($C_1$–$C_6$)alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:

in said groups of formula (II) at least one of the following applies:
1) a=0, y=0, and said linker D is bonded to the nitrogen atom that is bonded to E and L;
2) a=0, y=1, E, G, J, and L are carbon atoms, and said linker D and $R_5$ are bonded to the nitrogen atom that is bonded to E and L;
3) a=0, y=1, at least one of said ring members E, G, J, and L is a nitrogen atom to which $R_5$ is bonded, and said linker D is bonded to the nitrogen atom that is bonded to E and L
4) a=1, y=0, said linker D is bonded to one of said ring members chosen from E, G, J and L;
5) a=1, y=1, said ring members E, G, J, and L are carbon atoms one of which is bonded to said linker D, and $R_5$ is bonded to the nitrogen atom that is bonded to E and L; and
6) a=1, y=1, said linker D is bonded to one of said ring members chosen from E, G, J and L, and at least one of said ring members E, G, J, and L is a nitrogen atom to which $R_5$ is bonded;

in said groups of formula (III) at least one of the following applies:
1) a=0, y=0, said linker D is bonded to the nitrogen atom that is bonded to E and M;
2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:
1) a=0, y=0 or 1, said linker D is bonded to the nitrogen that is bonded to groups $R_6$, $R_7$, and $R_8$;
2) a=1, y=0 or 1, two of the groups $R_6$, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

$X^-$ is chosen from monovalent anions and divalent anions;

provided that said compounds of formula (I) comprise at least one group Z;

(3) ($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$)alkylamino($C_1$–$C_6$)alkylcarbonyl groups, N,N-di($C_1$–$C_6$)alkylamino($C_1$–$C_6$)alkylcarbonyl groups, amino($C_1$–$C_6$)alkylcarbonyl($C_1$–$C_6$)alkyl groups, N—Z-amino($C_1$–$C_6$)alkylcarbonyl($C_1$–$C_6$)alkyl groups, N—($C_1$–$C_6$)alkylamino($C_1$–$C_6$)alkylcarbonyl($C_1$–$C_6$)alkyl groups, N,N-di($C_1$–$C_6$)alkylamino($C_1$–$C_6$)alkylcarbonyl($C_1$–$C_6$)alkyl groups, carboxyl groups, ($C_1$–$C_6$)alkylcarboxyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$)alkylaminosulfonyl groups, $C_1$–$C_6$aminosulfonylalkyl groups, $C_1$–$C_6$N—Z-aminosulfonylalkyl groups, N—($C_1$–$C_6$)alkylaminosulfonyl($C_1$–$C_6$)alkyl groups, N,N-di($C_1$–$C_6$)alkylaminosulfonyl($C_1$–$C_6$)alkyl groups, carbamyl groups, N—($C_1$–$C_6$)alkylcarbamyl groups, N,N-di($C_1$–$C_6$)alkylcarbamyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, $C_1$–$C_6$trifluoroalkyl groups, and cyano groups, wherein Z is defined above;

(4) groups —$OR_4$ and groups —$SR_4$, wherein said $R_4$ are chosen from:
$C_1$–$C_6$alkyl groups, $C_1$–$C_6$monohydroxyalkyl groups, and $C_2$–$C_6$polyhydroxyalkyl groups, groups Z as defined above, ($C_1$–$C_6$)alkoxy($C_1$–$C_6$)alkyl groups, aryl groups, benzyl groups, carboxy($C_1$–$C_6$)alkyl groups, ($C_1$–$C_6$)alkylcarboxy($C_1$–$C_6$)alkyl groups, cyano($C_1$–$C_6$)alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$trifluoroalkyl groups, $C_1$–$C_6$aminosulfonylalkyl groups, $C_1$–$C_6$N—Z-aminosulfonylalkyl groups, N—($C_1$–$C_6$)alkylaminosulfonyl($C_1$–$C_6$)alkyl groups, N,N-di($C_1$–$C_6$)alkylaminosulfonyl($C_1$–$C_6$)alkyl groups, ($C_1$–$C_6$)alkylsulfinyl($C_1$–$C_6$)alkyl groups, ($C_1$–$C_6$)alkylsulfonyl($C_1$–$C_6$)alkyl groups, ($C_1$–$C_6$)alkylcarbonyl($C_1$–$C_6$)alkyl groups, $C_1$–$C_6$aminoalkyl groups, wherein the alkyl is optionally substituted with at least one hydroxyl group, $C_1$–$C_6$aminoalkyl groups, wherein said alkyl is unsubstituted or substituted with at least one hydroxyl group and, wherein said amine is substituted with one or two groups, which may be identical or different, each chosen from $C_1$–$C_6$alkyl groups, $C_1$–$C_6$monohydroxyalkyl groups, $C_2$–$C_6$polyhydroxyalkyl groups, ($C_1$–$C_6$)alkylcarbonyl groups, formyl groups, trifluoro($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, thiocarbamyl groups and $C_1$–$C_6$alkylsulfonyl groups and groups Z as defined above, and, when said amine is substituted with two groups, said two groups may optionally form, together with the nitrogen atom to which said two groups are commonly bonded, at least one ring chosen from 5- and 6-membered carbon-based rings and rings comprising at least one hetero atom;

(5) amino groups protected with at least one group chosen from
($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$)alkylamino($C_1$–$C_6$)alkylcarbonyl groups, N,N-di ($C_1$–$C_6$)alkylamino($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$)alkylaminosulfonyl groups, thiocarbamyl groups, formyl groups, and groups Z as defined above wherein said linker D in said groups Z comprises at least one ketone functional group directly bonded to the nitrogen atom of said amino group;

(6) $C_1$–$C_6$aminoalkyl groups, wherein the alkyl is optionally substituted with at least one hydroxyl group;

(7) amino($C_1$–$C_6$)alkyl groups, wherein the alkyl is optionally substituted with at least one hydroxyl group and wherein said amino is substituted with one or two groups, which may be identical or different, chosen from alkyl groups, $C_1$–$C_6$monohydroxyalkyl groups, $C_2$–$C_6$polyhydroxyalkyl groups, ($C_1$–$C_6$)alkylcarbonyl groups, carbamyl groups, N—($C_1$–$C_6$)alkylcarbamyl groups, N,N-di($C_1$–$C_6$)alkylcarbamyl groups, ($C_1$–$C_6$)alkylsulfonyl groups, formyl groups, trifluoro($C_1$–$C_6$)alkylcarbonyl groups, ($C_1$–$C_6$)alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom; and (B) developing a color with at least one oxidizing agent, wherein said oxidizing agent is combined at the time of use with said at least one dyeing composition or said at least one oxidizing agent is applied simultaneously with or sequentially to said at least one dyeing composition.

60. A composition according to claim 59, wherein said keratin fibers are human hair.

61. A process according to claim 59, wherein said at least one oxidizing agent is chosen from hydrogen peroxide, urea peroxide, alkali metal bromates, persalts, and enzymes.

62. A process according to claim 61, wherein said persalts are chosen from perborates and persulfates.

63. A process according to claim 61, wherein said enzymes are chosen from peroxidases, laccases, tyrosinases and oxidoreductases.

64. A process according to claim 63, wherein said oxidoreductases are chosen from pyranose oxidases, glucose oxidases, glycerol oxidases, lactate oxidases, pyruvate oxidases and uricases.

65. A process for oxidation dyeing keratin fibers comprising (A) applying to said keratin fibers at least one dyeing composition comprising, in a medium appropriate for dyeing:

at least one coloring compound chosen from oxidation bases and acid addition salts of said oxidation bases, and at least one coupler chosen from compounds of formula (I) below and acid addition salts thereof:

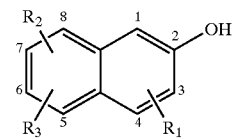

wherein:

groups $R_1$, $R_2$ and $R_3$, which may be identical or different, are each chosen from:
(1) a hydrogen and a halogen atom;
(2) groups Z chosen from groups of formulae (II), (III), and (IV):

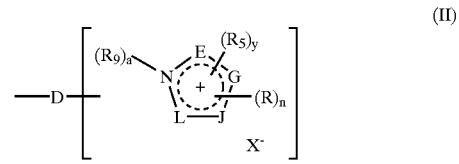

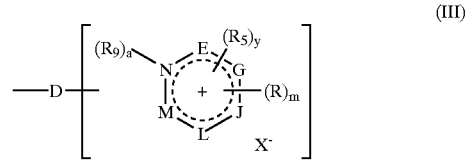

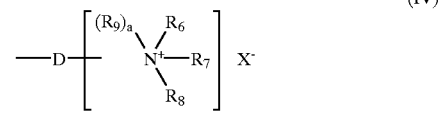

wherein:

linker D is chosen from linear and branched divalent alkylene groups, optionally comprising at least one hetero atom, and optionally substituted with at least one group chosen from hydroxyl groups and $C_1$–$C_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;

m is an integer ranging from 0 to 5;

R, which may be identical or different, are each chosen from:
    groups Z, as defined above;
    a halogen atom, a hydroxyl group, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$)alkylsilane ($C_1$–$C_6$)alkyl groups, amido groups, aldehydo groups, carboxyl groups, ($C_1$–$C_6$)alkylcarbonyl groups, thio groups, $C_1$–$C_6$thioalkyl groups, $C_1$–$C_6$alkylthio groups, amino groups optionally protected with at least one group chosen from ($C_1$–$C_6$)alkylcarbonyl groups, carbamyl groups and $C_1$–$C_6$alkylsulfonyl groups, groups $NHR^2$ and $NR^2R'''$ in which $R^2$ and $R'''$, which may be identical or different, are each chosen from $C_1$–$C_6$alkyl groups, $C_1$–$C_6$monohydroxyalkyl groups and $C_2$–$C_6$polyhydroxyalkyl groups;

$R_5$ is chosen from $C_1$–$C_6$alkyl groups, $C_1$–$C_6$monohydroxyalkyl groups, $C_2$–$C_6$polyhydroxyalkyl groups, cyano($C_1$–$C_6$) alkyl groups, tri($C_1$–$C_6$)alkylsilane($C_1$–$C_6$)alkyl groups, ($C_1$–$C_6$)alkoxy($C_1$–$C_6$)alkyl groups, carbamyl($C_1$–$C_6$)alkyl groups, ($C_1$–$C_6$) alkylcarboxy($C_1$–$C_6$)alkyl groups, benzyl groups, and groups Z, as defined above;

$R_6$, $R_7$ and $R_8$, which may be identical or different, are each chosen from:

$C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, cyano ($C_1$–$C_6$)alkyl groups, aryl groups, benzyl groups, $C_1$–$C_6$amidoalkyl groups, tri($C_1$–$C_6$) alkylsilane($C_1$–$C_6$)alkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups;

two of the groups $R_6$, $R_7$ and $R_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$ alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:

$C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:

in said groups of formula (II) at least one of the following applies:

1) a=0, y=0, and said linker D is bonded to the nitrogen atom that is bonded to E and L;
2) a=0, y=1, E, G, J, and L are carbon atoms, and said linker D and $R_5$ are bonded to the nitrogen atom that is bonded to E and L;
3) a=0, y=1, at least one of said ring members E, G, J, and L is a nitrogen atom to which $R_5$ is bonded, and said linker D is bonded to the nitrogen atom that is bonded to E and L;
4) a=1, y=0, said linker D is bonded to one of said ring members chosen from E, G, J and L;
5) a=1, y=1, said ring members E, G, J, and L are carbon atoms one of which is bonded to said linker D, and $R_5$ is bonded to the nitrogen atom that is bonded to E and L; and
6) a=1, y=1, said linker D is bonded to one of said ring members chosen from E, G, J and L, and at least one of said ring members E, G, J, and L is a nitrogen atom to which $R_5$ is bonded;

in said groups of formula (III) at least one of the following applies:

1) a=0, y=0, said linker D is bonded to the nitrogen atom that is bonded to E and M;
2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:

1) a=0, y=0 or 1, said linker D is bonded to the nitrogen that is bonded to groups $R_6$, $R_7$, and $R_8$;
2) a=1, y=0 or 1, two of the groups $R_6$, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

$X^-$ is chosen from monovalent anions and divalent anions;

provided that said compounds of formula (I) comprise at least one group Z;

(3) ($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino ($C_1$–$C_6$)alkylcarbonyl groups, N,N-di($C_1$–$C_6$) alkylamino($C_1$–Cr)alkylcarbonyl groups, amino ($C_1$–$C_6$)alkylcarbonyl($C_1$–$C_6$)alkyl groups, N—Z-amino($C_1$–$C_6$)alkylcarbonyl($C_1$–$C_6$)alkyl groups, N—($C_1$–$C_6$)alkylamino($C_1$–$C_6$)alkylcarbonyl ($C_1$–$C_6$)alkyl groups, N,N-di($C_1$–$C_6$)alkylamino ($C_1$–$C_6$)alkylcarbonyl($C_1$–$C_6$)alkyl groups, carboxyl groups, ($C_1$–$C_6$)alkylcarboxyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$) alkylaminosulfonyl groups, $C_1$–$C_6$aminosulfonylalkyl groups, $C_1$–$C_6$N—Z-aminosulfonylalkyl groups, N—($C_1$–$C_6$) alkylaminosulfonyl($C_1$–$C_6$)alkyl groups, N,N-di ($C_1$–$C_6$)alkylaminosulfonyl($C_1$–$C_6$)alkyl groups, carbamyl groups, N—($C_1$–$C_6$)alkylcarbamyl groups, N,N-di($C_1$–$C_6$)alkylcarbamyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, $C_1$–$C_6$alkyl groups, $C_1$–$C_6$monohydroxyalkyl groups, $C_2$–$C_6$polyhydroxyalkyl groups, ($C_1$–$C_6$)alkoxy ($C_1$–$C_6$)alkyl groups, $C_1$–$C_6$trifluoroalkyl groups, and cyano groups, wherein Z is defined above;

(4) groups —$OR_4$ and groups —$SR_4$, wherein said $R_4$ are chosen from:

$C_1$–$C_6$alkyl groups, $C_1$–$C_6$monohydroxyalkyl groups, and $C_2$–$C_6$polyhydroxyalkyl groups, groups Z as defined above, ($C_1$–$C_6$)alkoxy ($C_1$–$C_6$)alkyl groups, aryl groups, benzyl groups, carboxy($C_1$–$C_6$)alkyl groups, ($C_1$–$C_6$) alkylcarboxy($C_1$–$C_6$)alkyl groups, cyano($C_1$–$C_6$) alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$trifluoroalkyl groups, $C_1$–$C_6$aminosulfonylalkyl groups, $C_1$–$C_6$N—Z—aminosulfonylalkyl groups, N—($C_1$–$C_6$) alkylaminosulfonyl($C_1$–$C_6$)alkyl groups, N,N-di ($C_1$–$C_6$)alkylaminosulfonyl($C_1$–$C_6$)alkyl groups, ($C_1$–$C_6$)alkylsulfinyl($C_1$–$C_6$)alkyl groups, ($C_1$–$C_6$)alkylsulfonyl($C_1$–$C_6$)alkyl groups, ($C_1$–$C_6$)alkylcarbonyl($C_1$–$C_6$)alkyl groups, $C_1$–$C_6$aminoalkyl groups, wherein the alkyl is optionally substituted with at least one hydroxyl group, $C_1$–$C_6$aminoalkyl groups, wherein said alkyl is unsubstituted or substituted with at least one hydroxyl group and, wherein said amine is substituted with one or two groups, which may be identical or different, each chosen from $C_1$–$C_6$alkyl groups, $C_1$–$C_6$monohydroxyalkyl groups, $C_2$–$C_6$polyhydroxyalkyl groups, ($C_1$–$C_6$) alkylcarbonyl groups, formyl groups, trifluoro ($C_1$–$C_6$)alkylcarbonyl groups, ($C_1$–$C_6$) alkylcarboxyl groups, carbamyl groups, N—($C_1$–$C_6$)alkylcarbamyl groups, N,N-di ($C_1$–$C_6$)alkylcarbamyl groups, thiocarbamyl groups and $C_1$–$C_6$alkylsulfonyl groups and groups Z as defined above, and, when said amine is substituted with two groups, said two groups may optionally form, together with the nitrogen atom to which said two groups are commonly bonded, at least one ring chosen from 5- and 6-membered carbon-based rings and rings comprising at least one hetero atom;

(5) amino groups protected with at least one group chosen from ($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino ($C_1$–$C_6$)alkylcarbonyl groups, N—($C_1$–$C_6$) alkylamino($C_1$–$C_6$)alkylcarbonyl groups, N,N-di ($C_1$–$C_6$)alkylamino($C_1$–$C_6$)alkylcarbonyl groups, ($C_1$–$C_6$)alkylcarboxyl groups, carbamyl groups, N—($C_1$–$C_6$)alkylcarbamyl groups, N,N-di ($C_1$–$C_6$)alkylcarbamyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$) alkylaminosulfonyl groups, thiocarbamyl groups, formyl groups, and groups Z as defined above wherein said linker D in said groups Z comprises at least one ketone functional group directly bonded to the nitrogen atom of said amino group;

(6) $C_1$–$C_6$aminoalkyl groups, wherein the alkyl is optionally substituted with at least one hydroxyl group;

(7) amino($C_1$–$C_6$)alkyl groups, wherein the alkyl is optionally substituted with at least one hydroxyl group and wherein said amino is substituted with one or two groups, which may be identical or different, chosen from alkyl groups, $C_1$–$C_6$monohydroxyalkyl groups, $C_2$–$C_6$polyhydroxyalkyl groups, ($C_1$–$C_6$) alkylcarbonyl groups, carbamyl groups, N—($C_1$–$C_6$) alkylcarbamyl groups, N,N-di($C_1$–$C_6$)alkylcarbamyl groups, ($C_1$–$C_6$)alkylsulfonyl groups, formyl groups, trifluoro($C_1$–$C_6$)alkylcarbonyl groups, ($C_1$–$C_6$) alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom; and (B) developing a color with at least one oxidizing agent present in an amount sufficient to develop a color, wherein said at least one oxidizing agent is combined at the time of use with said at least one dyeing composition, (C) leaving said combination to act for a time ranging from 3 to 50 minutes, and (D) rinsing said keratinous fibers, shampooing said keratinous fibers after said shampooing, and drying said keratinous fibers.

66. A process according to claim 65, wherein said keratin fibers are human hair.

67. A process according to claim 65, wherein said at least one oxidizing agent is chosen from hydrogen peroxide, urea peroxide, alkali metal bromates, persalts, and enzymes.

68. A process according to claim 67, wherein said persalts are chosen from perborates and persulfates.

69. A process according to claim 67, wherein said enzymes are chosen from peroxidases, laccases, tyrosinases, and oxidoreductases.

70. A process according to claim 69, wherein said oxidoreductases are chosen from pyranose oxidases, glucose oxidases, glycerol oxidases, lactate oxidases, pyruvate oxidases and uricases.

71. A kit comprising two compartments, wherein:

(a) a first compartment comprises at least one dyeing composition comprising, in a medium suitable for dyeing:

at least one coloring compound chosen from oxidation bases and acid addition salts of said oxidation bases, and at least one coupler chosen from compounds of formula (I) below and acid addition salts thereof:

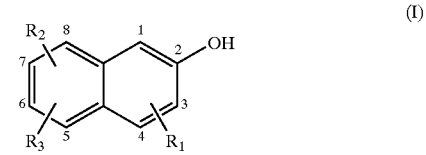

(I)

wherein:

groups $R_1$, $R_2$ and $R_3$, which may be identical or different, are each chosen from:

(1) a hydrogen and a halogen atom;

(2) groups Z chosen from groups of formulae (II), (III), and (IV):

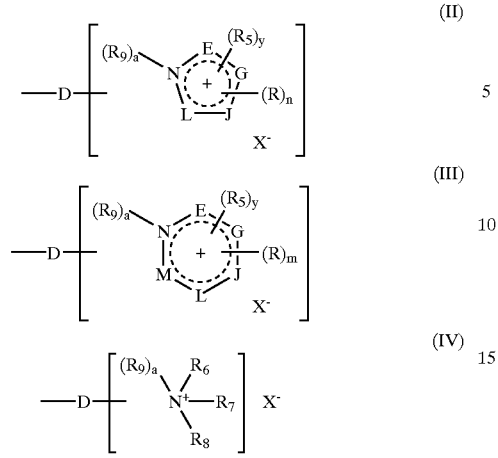

wherein:
linker D is chosen from linear and branched divalent alkylene groups, optionally comprising at least one hetero atom, and optionally substituted with at least one group chosen from hydroxyl groups and $C_1$–$C_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;

m is an integer ranging from 0 to 5;

R, which may be identical or different, are each chosen from:
groups Z, as defined above;
a halogen atom, a hydroxyl group, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$)alkylsilane($C_1$–$C_6$)alkyl groups, amido groups, aldehydo groups, carboxyl groups, ($C_1$–$C_6$) alkylcarbonyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups, groups $NHR^2$ and $NR^2R'''$ in which $R^2$ and $R'''$, which may be identical or different, are each chosen from $C_1$–$C_6$alkyl groups, $C_1$–$C_6$monohydroxyalkyl groups and $C_2$–$C_6$polyhydroxyalkyl groups;

$R_5$ is chosen from $C_1$–$C_6$alkyl groups, $C_1$–$C_6$monohydroxyalkyl groups, $C_2$–$C_6$polyhydroxyalkyl groups, cyano($C_1$–$C_6$) alkyl groups, tri($C_1$–$C_6$)alkylsilane($C_1$–$C_6$)alkyl groups, ($C_1$–$C_6$)alkoxy($C_1$–$C_6$)alkyl groups, carbamyl($C_1$–$C_6$)alkyl groups, ($C_1$–$C_6$) alkylcarboxy($C_1$–$C_6$)alkyl groups, benzyl groups, and groups Z, as defined above;

$R_6$, $R_7$ and $R_8$, which may be identical or different, are each chosen from:
$C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, cyano ($C_1$–$C_6$)alkyl groups, aryl groups, benzyl groups, $C_1$–$C_6$amidoalkyl groups, tri($C_1$–$C_6$) alkylsilane($C_1$–$C_6$)alkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups;

two of the groups $R_6$, $R_7$ and $R_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:
$C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl group, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:
in said groups of formula (II) at least one of the following applies:
1) a=0, y=0, and said linker D is bonded to the nitrogen atom that is bonded to E and L;
2) a=0, y=1, E, G, J, and L are carbon atoms, and said linker D and $R_5$ are bonded to the nitrogen atom that is bonded to E and L;
3) a=0, y=1, at least one of said ring members E, G, J, and L is a nitrogen atom to which $R_5$ is bonded, and said linker D is bonded to the nitrogen atom that is bonded to E and L;
4) a=1, y=0, said linker D is bonded to one of said ring members chosen from E, G, J and L;
5) a=1, y=1, said ring members E, G, J, and L are carbon atoms one of which is bonded to said linker D, and $R_5$ is bonded to the nitrogen atom that is bonded to E and L; and
6) a=1, y=1, said linker D is bonded to one of said ring members chosen from E, G, J and L, and at least one of said ring members E, G, J, and L is a nitrogen atom to which $R_5$ is bonded;

in said groups of formula (III) at least one of the following applies:
1) a=0, y=0, said linker D is bonded to the nitrogen atom that is bonded to E and M;
2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:
1) a=0, y=0 or 1, said linker D is bonded to the nitrogen that is bonded to groups $R_6$, $R_7$, and $R_8$;
2) a=1, y=0 or 1, two of the groups R6, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

$X^-$ is chosen from monovalent anions and divalent anions;

provided that said compounds of formula (I) comprise at least one group Z;

(3) $(C_1-C_6)$alkylcarbonyl groups, amino$(C_1-C_6)$alkylcarbonyl groups, N—Z-amino$(C_1-C_6)$alkylcarbonyl groups, N—$(C_1-C_6)$alkylamino$(C_1-C_6)$alkylcarbonyl groups, N,N-di$(C_1-C_6)$alkylamino$(C_1-C_6)$alkylcarbonyl groups, amino$(C_1-C_6)$alkylcarbonyl$(C_1-C_6)$alkyl groups, N—Z-amino$(C_1-C_6)$alkylcarbonyl$(C_1-C_6)$alkyl groups, N—$(C_1-C_6)$alkylamino$(C_1-C_6)$alkylcarbonyl$(C_1-C_6)$alkyl groups, N,N-di$(C_1-C_6)$alkylamino$(C_1-C_6)$alkylcarbonyl$(C_1-C_6)$alkyl groups, carboxyl groups, $(C_1-C_6)$alkylcarboxyl groups, $C_1-C_6$alkylsulfonyl groups, aminosulfonyl groups, N—Z-aminosulfonyl groups, $C_1-C_6$N-alkylaminosulfonyl groups, N,N-di$(C_1-C_6)$alkylaminosulfonyl groups, $C_1-C_6$aminosulfonylalkyl groups, $C_1-C_6$N—Z-aminosulfonylalkyl groups, N—$(C_1-C_6)$alkylaminosulfonyl$(C_1-C_6)$alkyl groups, N,N-di$(C_1-C_6)$alkylaminosulfonyl$(C_1-C_6)$alkyl groups, carbamyl groups, N—$(C_1-C_6)$alkylcarbamyl groups, N,N-di$(C_1-C_6)$alkylcarbamyl groups, carbamyl$(C_1-C_6)$alkyl groups, N—$(C_1-C_6)$alkylcarbamyl$(C_1-C_6)$alkyl groups, N,N-di$(C_1-C_6)$alkylcarbamyl$(C_1-C_6)$alkyl groups, $C_1-C_6$alkyl groups, $C_1-C_6$monohydroxyalkyl groups, $C_2-C_6$polyhydroxyalkyl groups, $(C_1-C_6)$alkoxy$(C_1-C_6)$alkyl groups, $C_1-C_6$trifluoroalkyl groups, and cyano groups, wherein Z is defined above;

(4) groups —$OR_4$ and groups —$SR_4$, wherein said $R_4$ are chosen from:
$C_1-C_6$alkyl groups, $C_1-C_6$monohydroxyalkyl groups, and $C_2-C_6$polyhydroxyalkyl groups, groups Z as defined above, $(C_1-C_6)$alkoxy$(C_1-C_6)$alkyl groups, aryl groups, benzyl groups, carboxy$(C_1-C_6)$alkyl groups, $(C_1-C_6)$alkylcarboxy$(C_1-C_6)$alkyl groups, cyano$(C_1-C_6)$alkyl groups, carbamyl$(C_1-C_6)$alkyl groups, N—$(C_1-C_6)$alkylcarbamyl$(C_1-C_6)$alkyl groups, N,N-di$(C_1-C_6)$alkylcarbamyl$(C_1-C_6)$alkyl groups, $C_1-C_6$trifluoroalkyl groups, $C_1-C_6$aminosulfonylalkyl groups, $C_1-C_6$N—Z-aminosulfonylalkyl groups, N—$(C_1-C_6)$alkylaminosulfonyl$(C_1-C_6)$alkyl groups, N,N-di$(C_1-C_6)$alkylaminosulfonyl$(C_1-C_6)$alkyl groups, $(C_1-C_6)$alkylsulfinyl$(C_1-C_6)$alkyl groups, $(C_1-C_6)$alkylsulfonyl$(C_1-C_6)$alkyl groups, $(C_1-C_6)$alkylcarbonyl$(C_1-C_6)$alkyl groups, $C_1-C_6$aminoalkyl groups, wherein the alkyl is optionally substituted with at least one hydroxyl group, $C_1-C_6$aminoalkyl groups, wherein said alkyl is unsubstituted or substituted with at least one hydroxyl group and, wherein said amine is substituted with one or two groups, which may be identical or different, each chosen from $C_1-C_6$alkyl groups, $C_1-C_6$monohydroxyalkyl groups, $C_2-C_6$polyhydroxyalkyl groups, $(C_1-C_6)$alkylcarbonyl groups, formyl groups, trifluoro$(C_1-C_6)$alkylcarbonyl groups, $(C_1-C_6)$alkylcarboxyl groups, carbamyl groups, N—$(C_1-C_6)$alkylcarbamyl groups, N,N-di$(C_1-C_6)$alkylcarbamyl groups, thiocarbamyl groups and $C_1-C_6$alkylsulfonyl groups and groups Z as defined above, and, when said amine is substituted with two groups, said two groups may optionally form, together with the nitrogen atom to which said two groups are commonly bonded, at least one ring chosen from 5- and 6-membered carbon-based rings and rings comprising at least one hetero atom;

(5) amino groups protected with at least one group chosen from:
$(C_1-C_6)$alkylcarbonyl groups, $(C_1-C_6)$alkylcarboxyl groups, trifluoro$(C_1-C_6)$alkylcarbonyl groups, amino$(C_1-C_6)$alkylcarbonyl groups, N—Z-amino$(C_1-C_6)$alkylcarbonyl groups, N—$(C_1-C_6)$alkylamino$(C_1-C_6)$alkylcarbonyl groups, N,N-di$(C_1-C_6)$alkylamino$(C_1-C_6)$alkylcarbonyl groups, $(C_1-C_6)$alkylcarboxyl groups, carbamyl groups, N—$(C_1-C_6)$alkylcarbamyl groups, N,N-di$(C_1-C_6)$alkylcarbamyl groups, $C_1-C_6$alkylsulfonyl groups, aminosulfonyl groups, N—Z-aminosulfonyl groups, $C_1-C_6$N-alkylaminosulfonyl groups, N,N-di$(C_1-C_6)$alkylaminosulfonyl groups, thiocarbamyl groups, formyl groups, and groups Z as defined above wherein said linker D in said groups Z comprises at least one ketone functional group directly bonded to the nitrogen atom of said amino group;

(6) $C_1-C_6$aminoalkyl groups, wherein the alkyl is optionally substituted with at least one hydroxyl group;

(7) amino$(C_1-C_6)$alkyl groups, wherein the alkyl is optionally substituted with at least one hydroxyl group and wherein said amino is substituted with one or two groups, which may be identical or different, chosen from alkyl groups, $C_1-C_6$monohydroxyalkyl groups, $C_2-C_6$polyhydroxyalkyl groups, $(C_1-C_6)$alkylcarbonyl groups, carbamyl groups, N—$(C_1-C_6)$alkylcarbamyl groups, N,N-di$(C_1-C_6)$alkylcarbamyl groups, $(C_1-C_6)$alkylsulfonyl groups, formyl groups, trifluoro$(C_1-C_6)$alkylcarbonyl groups, $(C_1-C_6)$alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom; and (b) a second compartment comprises at least one oxidizing agent.

72. A compound of formula (I') or an acid addition salt thereof:

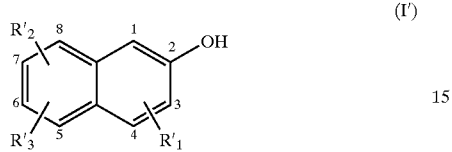

(I')

wherein:

$R'_1$, $R'_2$ and $R'_3$, which may be identical or different, are each chosen from:
(1) a hydrogen and a halogen atom;
(2) groups Z chosen from groups of formulae (II), (III), and (IV):

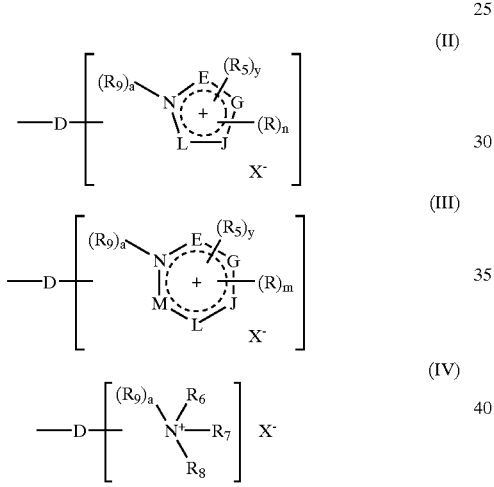

wherein:
linker D is chosen from linear and branched divalent alkylene groups, optionally comprising at least one hetero atom, and optionally substituted with at least one group chosen from hydroxyl groups and $C_1$–$C_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;
m is an integer ranging from 0 to 5;
R, which may be identical or different, are each chosen from:
groups Z, as defined above;
a halogen atom, a hydroxyl group, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$)alkylsilane($C_1$–$C_6$)alkyl groups, amido groups, aldehydo groups, carboxyl groups, ($C_1$–$C_6$) alkylcarbonyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups, groups $NHR^2$ and $NR^2R'''$ in which $R^2$ and $R'''$, which may be identical or different, are each chosen from $C_1$–$C_6$alkyl groups, $C_1$–$C_6$monohydroxyalkyl groups and $C_2$–$C_6$polyhydroxyalkyl groups;

$R_5$ is chosen from $C_1$–$C_6$alkyl groups, $C_1$–$C_6$monohydroxyalkyl groups, $C_2$–$C_6$polyhydroxyalkyl groups, cyano($C_1$–$C_6$) alkyl groups, tri($C_1$–$C_6$)alkylsilane($C_1$–$C_6$)alkyl groups, ($C_1$–$C_6$)alkoxy($C_1$–$C_6$)alkyl groups, carbamyl($C_1$–$C_6$)alkyl groups, ($C_1$–$C_6$) alkylcarboxy($C_1$–$C_6$)alkyl groups, benzyl groups, and groups Z, as defined above;

$R_6$, $R_7$ and $R_8$, which may be identical or different, are each chosen from:
$C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, cyano ($C_1$–$C_6$)alkyl groups, aryl groups, benzyl groups, $C_1$–$C_6$amidoalkyl groups, tri($C_1$–$C_6$) alkylsilane($C_1$–$C_6$)alkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups;

two of the groups $R_6$, $R_7$ and $R_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:
$C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$) alkylketo($C_1$–$C_6$)alkyl groups, N—($C_1$–$C_6$)

alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:

in said groups of formula (II) at least one of the following applies:
1) a=0, y=0, and said linker D is bonded to the nitrogen atom that is bonded to E and L;
2) a=0, y=1, E, G, J, and L are carbon atoms, and said linker D and $R_5$ are bonded to the nitrogen atom that is bonded to E and L;
3) a=0, y=1, at least one of said ring members E, G, J, and L is a nitrogen atom to which $R_5$ is bonded, and said linker D is bonded to the nitrogen atom that is bonded to E and L;
4) a=1, y=0, said linker D is bonded to one of said ring members chosen from E, G, J and L;
5) a=1, y=1, said ring members E, G, J, and L are carbon atoms one of which is bonded to said linker D, and $R_5$ is bonded to the nitrogen atom that is bonded to E and L; and
6) a=1, y=1, said linker D is bonded to one of said ring members chosen from E, G, J and L, and at least one of said ring members E, G, J, and L is a nitrogen atom to which $R_5$ is bonded;

in said groups of formula (III) at least one of the following applies:
1) a=0, y=0, said linker D is bonded to the nitrogen atom that is bonded to E and M;
2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:
1) a=0, y=0 or 1, said linker D is bonded to the nitrogen that is bonded to groups $R_6$, $R_7$, and $R_8$;
2) a=1, y=0 or 1, two of the groups $R_6$, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

$X^-$ is chosen from monovalent anions and divalent anions;

provided that said compounds of formula (I) comprise at least one group Z;

(3) ($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino ($C_1$–$C_6$)alkylcarbonyl groups, N,N-di($C_1$–$C_6$) alkylamino($C_1$–$C_6$)alkylcarbonyl groups, amino ($C_1$–$C_6$)alkylcarbonyl($C_1$–$C_6$)alkyl groups, N—Z-amino($C_1$–$C_6$)alkylcarbonyl($C_1$–$C_6$)alkyl groups, N—($C_1$–$C_6$)alkylamino($C_1$–$C_6$)alkylcarbonyl ($C_1$–$C_6$)alkyl groups, N,N-di($C_1$–$C_6$)alkylamino ($C_1$–$C_6$)alkylcarbonyl($C_1$–$C_6$)alkyl groups, carboxyl groups, ($C_1$–$C_6$)alkylcarboxyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$) alkylaminosulfonyl groups, $C_1$–$C_6$aminosulfonylalkyl groups, $C_1$–$C_6$N—Z-aminosulfonylalkyl groups, N—($C_1$–$C_6$) alkylaminosulfonyl($C_1$–$C_6$)alkyl groups, N,N-di ($C_1$–$C_6$)alkylaminosulfonyl($C_1$–$C_6$)alkyl groups, carbamyl groups, N—($C_1$–$C_6$)alkylcarbamyl groups, N,N-di($C_1$–$C_6$)alkylcarbamyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, $C_1$–$C_6$alkyl groups, $C_1$–$C_6$monohydroxyalkyl groups, $C_2$–$C_6$polyhydroxyalkyl groups, ($C_1$–$C_6$)alkoxy ($C_1$–$C_6$)alkyl groups, $C_1$–$C_6$trifluoroalkyl groups, and cyano groups, wherein Z is defined above;

(4) groups —$OR_4$ and groups —$SR_4$, wherein said $R_4$ are chosen from:
$C_1$–$C_6$alkyl groups, $C_1$–$C_6$monohydroxyalkyl groups, and $C_2$–$C_6$polyhydroxyalkyl groups, groups Z as defined above, ($C_1$–$C_6$)alkoxy ($C_1$–$C_6$)alkyl groups, aryl groups, benzyl groups, carboxy($C_1$–$C_6$)alkyl groups, ($C_1$–$C_6$) alkylcarboxy($C_1$–$C_6$)alkyl groups, cyano($C_1$–$C_6$) alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$trifluoroalkyl groups, $C_1$–$C_6$aminosulfonylalkyl groups, $C_1$–$C_6$N—Z-aminosulfonylalkyl groups, N—($C_1$–$C_6$) alkylaminosulfonyl($C_1$–$C_6$)alkyl groups, N,N-di ($C_1$–$C_6$)alkylaminosulfonyl($C_1$–$C_6$)alkyl groups, ($C_1$–$C_6$)alkylsulfinyl($C_1$–$C_6$)alkyl groups, ($C_1$–$C_6$)alkylsulfonyl($C_1$–$C_6$)alkyl groups, ($C_1$–$C_6$)alkylcarbonyl($C_1$–$C_6$)alkyl groups, $C_1$–$C_6$aminoalkyl groups, wherein the alkyl is optionally substituted with at least one hydroxyl group, $C_1$–$C_6$aminoalkyl groups, wherein said alkyl is unsubstituted or substituted with at least one hydroxyl group and, wherein said amine is substituted with one or two groups, which may be identical or different, each chosen from $C_1$–$C_6$alkyl groups, $C_1$–$C_6$monohydroxyalkyl groups, $C_2$–$C_6$polyhydroxyalkyl groups, ($C_1$–$C_6$) alkylcarbonyl groups, formyl groups, trifluoro ($C_1$–$C_6$)alkylcarbonyl groups, ($C_1$–$C_6$) alkylcarboxyl groups, carbamyl groups, N—($C_1$–$C_6$)alkylcarbamyl groups, N,N-di ($C_1$–$C_6$)alkylcarbamyl groups, thiocarbamyl groups and $C_1$–$C_6$alkylsulfonyl groups and groups Z as defined above, and, when said amine is substituted with two groups, said two groups may optionally form, together with the nitrogen atom to which said two groups are commonly bonded, at least one ring chosen from 5- and 6-membered carbon-based rings and rings comprising at least one hetero atom;

(5) amino groups protected with at least one group chosen from
($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino ($C_1$–$C_6$)alkylcarbonyl groups, N—($C_1$–$C_6$) alkylamino($C_1$–$C_6$)alkylcarbonyl groups, N,N-di ($C_1$–$C_6$)alkylamino($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$)alkylaminosulfonyl groups, thiocarbamyl groups, formyl groups, and groups Z as defined above wherein said linker D in said groups Z comprises at least one ketone functional group directly bonded to the nitrogen atom of said amino group;

(6) $C_1$–$C_6$aminoalkyl groups, wherein the alkyl is optionally substituted with at least one hydroxyl group;

(7) amino($C_1$–$C_6$)alkyl groups, wherein the alkyl is optionally substituted with at least one hydroxyl group and wherein said amino is substituted with one or two groups, which may be identical or different, chosen from alkyl groups, $C_1$–$C_6$monohydroxyalkyl groups, $C_2$–$C_6$polyhydroxyalkyl groups, ($C_1$–$C_6$) alkylcarbonyl groups, carbamyl groups, N—($C_1$–$C_6$) alkylcarbamyl groups, N,N-di($C_1$–$C_6$)alkylcarbamyl groups, ($C_1$–$C_6$)alkylsulfonyl groups, formyl groups, trifluoro($C_1$–$C_6$)alkylcarbonyl groups, ($C_1$–$C_6$) alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom; and provided that when two of $R'_1$, $R'_2$, and $R'_3$ simultaneously are a hydrogen atom, and when the other group $R'_1$, $R'_2$, and $R'_3$ is a group comprising a functional group chosen from amido and carboxyl functional groups, then said amido and carboxyl functional group is not directly bonded to the naphthol ring system;

and further excluding:

6-hydroxy-N,N,N-trimethyl-1-naphthalenemethanaminium chloride; and

[(2-hydroxy-1-naphthyl)methyl]trimethylammonium iodide.

73. A process for dyeing keratin fibers comprising applying to said keratin fibers at least one coupler chosen from compounds of formula (I') and acid addition salts thereof:

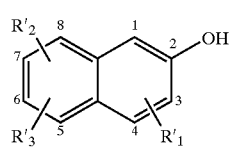

(I')

wherein:

$R'_1$, $R'_2$ and $R'_3$, which may be identical or different, are each chosen from:
(1) a hydrogen and a halogen atom;
(2) groups Z chosen from groups of formulae (II), (III), and (IV):

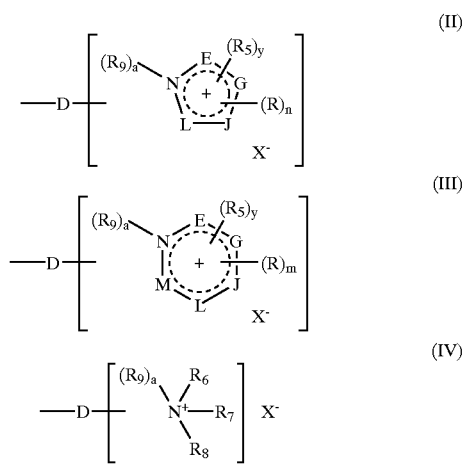

wherein:

linker D is chosen from linear and branched divalent alkylene groups, optionally comprising at least one hetero atom, and optionally substituted with at least one group chosen from hydroxyl groups and $C_1$–$C_6$alkoxy groups, and optionally comprising at least one ketone functional group;

E, G, J, L and M, which may be identical or different, are each an atom chosen from carbon, oxygen, sulfur, and nitrogen;

n is an integer ranging from 0 to 4;

m is an integer ranging from 0 to 5;

R, which may be identical or different, are each chosen from:
groups Z, as defined above;
a halogen atom, a hydroxyl group, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$)alkylsilane ($C_1$–$C_6$)alkyl groups, amido groups, aldehydo groups, carboxyl groups, ($C_1$–$C_6$) alkylcarbonyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups, groups $NHR^2$ and $NR^2R'''$ in which $R^2$ and $R'''$, which may be identical or different, are each chosen from $C_1$–$C_6$alkyl groups, $C_1$–$C_6$monohydroxyalkyl groups and $C_2$–$C_6$polyhydroxyalkyl groups;

$R_5$ is chosen from $C_1$–$C_6$alkyl groups, $C_1$–$C_6$monohydroxyalkyl groups, $C_2$–$C_6$polyhydroxyalkyl groups, cyano($C_1$–$C_6$) alkyl groups, tri($C_1$–$C_6$)alkylsilane($C_1$–$C_6$)alkyl groups, ($C_1$–$C_6$)alkoxy($C_1$–$C_6$)alkyl groups, carbamyl($C_1$–$C_6$)alkyl groups, ($C_1$–$C_6$) alkylcarboxy($C_1$–$C_6$)alkyl groups, benzyl groups, and groups Z, as defined above;

$R_6$, $R_7$ and $R_8$, which may be identical or different, are each chosen from:
$C_1$–$C_6$alkyl groups, $C_1$–$C_6$monohydroxyalkyl groups, $C_2$–$C_6$polyhydroxyalkyl groups, ($C_1$–$C_6$)alkoxy($C_1$–$C_6$)alkyl groups, cyano ($C_1$–$C_6$)alkyl groups, aryl groups, benzyl groups, $C_1$–$C_6$amidoalkyl groups, tri($C_1$–$C_6$) alkylsilane($C_1$–$C_6$)alkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups;

two of the groups $R_6$, $R_7$ and $R_8$ can together also form, with the nitrogen atom to which said two groups are commonly bonded, at least one saturated ring chosen from 5- and 6-membered carbon-based rings comprising at least one hetero atom, it being possible for said at least one ring to be substituted with at least one unit chosen from halogen atoms, hydroxyl groups, $C_1$–$C_6$alkyl groups, $C_1$–$C_6$monohydroxyalkyl groups, $C_2$–$C_6$polyhydroxyalkyl groups, nitro groups, cyano groups, cyano($C_1$–$C_6$)alkyl groups, $C_1$–$C_6$alkoxy groups, tri($C_1$–$C_6$) alkylsilane($C_1$–$C_6$)alkyl groups, amido groups, aldehydo groups, carboxyl groups, keto ($C_1$–$C_6$)alkyl groups, thio groups, $C_1$–$C_6$thioalkyl groups, $C_1$–$C_6$alkylthio groups, amino groups optionally protected with at least one group chosen from ($C_1$–$C_6$) alkylcarbonyl groups, carbamyl groups and $C_1$–$C_6$alkylsulfonyl groups and groups Z, as defined above;

$R_9$ is a group chosen from:

$C_1$–$C_6$alkyl groups, $C_1$–$C_6$monohydroxyalkyl groups, $C_2$–$C_6$polyhydroxyalkyl groups, aryl groups, benzyl groups, $C_1$–$C_6$aminoalkyl groups, $C_1$–$C_6$aminoalkyl groups, wherein the amine is protected with at least one group chosen from ($C_1$–$C_6$)alkylcarbonyl groups, carbamyl groups and $C_1$–$C_6$alkylsulfonyl groups, carboxy($C_1$–$C_6$)alkyl groups, cyano ($C_1$–$C_6$)alkyl groups, carbamyl($C_1$–$C_6$)alkyl groups, $C_1$–$C_6$trifluoroalkyl groups, tri($C_1$–$C_6$) alkylsilane($C_1$–$C_6$)alkyl groups, $C_1$–$C_6$sulfonamidoalkyl groups, ($C_1$–$C_6$) alkylcarboxy($C_1$–$C_6$)alkyl groups, ($C_1$–$C_6$) alkylsulfinyl($C_1$–$C_6$)alkyl groups, ($C_1$–$C_6$) alkylsulfonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, and N—($C_1$–$C_6$)alkylsulfonamido($C_1$–$C_6$)alkyl groups;

a and y, which may be identical or different, are each chosen from 0 and 1, provided that:

in said groups of formula (II) at least one of the following applies:
1) a=0, y=0, and said linker D is bonded to the nitrogen atom that is bonded to E and L;
2) a=0, y=1, E, G, J, and L are carbon atoms, and said linker D and $R_5$ are bonded to the nitrogen atom that is bonded to E and L;
3) a=0, y=1, at least one of said ring members E, G, J, and L is a nitrogen atom to which $R_5$ is bonded, and said linker D is bonded to the nitrogen atom that is bonded to E and L;
4) a=1, y=0, said linker D is bonded to one of said ring members chosen from E, G, J and L;
5) a=1, y=1, said ring members E, G, J, and L are carbon atoms one of which is bonded to said linker D, and $R_5$ is bonded to the nitrogen atom that is bonded to E and L; and
6) a=1, y=1, said linker D is bonded to one of said ring members chosen from E, G, J and L, and at least one of said ring members E, G, J, and L is a nitrogen atom to which $R_5$ is bonded;

in said groups of formula (III) at least one of the following applies:
1) a=0, y=0, said linker D is bonded to the nitrogen atom that is bonded to E and M;
2) a=0, y=1, said linker D and said $R_5$ are bonded to the nitrogen atom that is bonded to E and L, and at least one of said ring members E, G, J, L, and M is chosen from divalent atoms;
3) a=1, y=0, said linker D is bonded to a said ring member chosen from E, G, J, L, and M;
4) a=1, y=1, at least one of said ring members E, G, J, L, and M is chosen from divalent atoms one of which is bonded to said linker D, and said $R_5$ is bonded to the nitrogen atom that is bonded to E and M;

in said groups of formula (IV) at least one of the following applies:
1) a=0, y=0 or 1, said linker D is bonded to the nitrogen that is bonded to groups $R_6$, $R_7$, and $R_8$;
2) a=1, y=0 or 1, two of the groups $R_6$, $R_7$, and $R_8$ form, together with the nitrogen atom to which said groups are commonly bonded, at least one saturated ring chosen from 5- and 6-membered rings as defined above, and said linker D is bonded to a carbon atom of said at least one saturated ring;

$X^-$ is chosen from monovalent anions and divalent anions;

provided that said compounds of formula (I) comprise at least one group Z;

(3) ($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino ($C_1$–$C_6$)alkylcarbonyl groups, N,N-di($C_1$–$C_6$) alkylamino($C_1$–$C_6$)alkylcarbonyl groups, amino ($C_1$–$C_6$)alkylcarbonyl($C_1$–$C_6$)alkyl groups, N—Z-amino($C_1$–$C_6$)alkylcarbonyl($C_1$–$C_6$)alkyl groups, N—($C_1$–$C_6$)alkylamino($C_1$–$C_6$)alkylcarbonyl ($C_1$–$C_6$)alkyl groups, N,N-di($C_1$–$C_6$)alkylamino ($C_1$–$C_6$)alkylcarbonyl($C_1$–$C_6$)alkyl groups, carboxyl groups, ($C_1$–$C_6$)alkylcarboxyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$) alkylaminosulfonyl groups, $C_1$–$C_6$aminosulfonylalkyl groups, $C_1$–$C_6$N—Z-aminosulfonylalkyl groups, N—($C_1$–$C_6$) alkylaminosulfonyl($C_1$–$C_6$)alkyl groups, N,N-di ($C_1$–$C_6$)alkylaminosulfonyl($C_1$–$C_6$)alkyl groups, carbamyl groups, N—($C_1$–$C_6$)alkylcarbamyl groups, N,N-di($C_1$–$C_6$)alkylcarbamyl groups, carbamyl ($C_1$–$C_6$)alkyl groups, N—($C_1$–$C_6$)alkylcarbamyl ($C_1$–$C_6$)alkyl groups, N,N-di($C_1$–$C_6$)alkylcarbamyl ($C_1$–$C_6$)alkyl groups, $C_1$–$C_6$alkyl groups, $C_1$–$C_6$monohydroxyalkyl groups, $C_2$–$C_6$polyhydroxyalkyl groups, ($C_1$–$C_6$)alkoxy ($C_1$–$C_6$)alkyl groups, $C_1$–$C_6$trifluoroalkyl groups, and cyano groups, wherein Z is defined above;

(4) groups —$OR_4$ and groups —$SR_4$, wherein said $R_4$ are chosen from:

$C_1$–$C_6$alkyl groups, $C_1$–$C_6$monohydroxyalkyl groups, and $C_2$–$C_6$polyhydroxyalkyl groups, groups Z as defined above, ($C_1$–$C_6$)alkoxy ($C_1$–$C_6$)alkyl groups, aryl groups, benzyl groups, carboxy($C_1$–$C_6$)alkyl groups, ($C_1$–$C_6$) alkylcarboxy($C_1$–$C_6$)alkyl groups, cyano($C_1$–$C_6$)

alkyl groups, carbamyl($C_1$–$C_6$)alkyl groups, N—($C_1$–$C_6$)alkylcarbamyl($C_1$–$C_6$)alkyl groups, N,N-di($C_1$–$C_6$)alkylcarbamyl($C_1$–$C_6$)alkyl groups, $C_1$–$C_6$trifluoroalkyl groups, $C_1$–$C_6$aminosulfonylalkyl groups, $C_1$–$C_6$N—Z—aminosulfonylalkyl groups, N—($C_1$–$C_6$)alkylaminosulfonyl($C_1$–$C_6$)alkyl groups, N,N-di($C_1$–$C_6$)alkylaminosulfonyl($C_1$–$C_6$)alkyl groups, ($C_1$–$C_6$)alkylsulfinyl($C_1$–$C_6$)alkyl groups, ($C_1$–$C_6$)alkylsulfonyl($C_1$–$C_6$)alkyl groups, ($C_1$–$C_6$)alkylcarbonyl($C_1$–$C_6$)alkyl groups, $C_1$–$C_6$aminoalkyl groups, wherein the alkyl is optionally substituted with at least one hydroxyl group, $C_1$–$C_6$aminoalkyl groups, wherein said alkyl is unsubstituted or substituted with at least one hydroxyl group and, wherein said amine is substituted with one or two groups, which may be identical or different, each chosen from $C_1$–$C_6$alkyl groups, $C_1$–$C_6$monohydroxyalkyl groups, $C_2$–$C_6$polyhydroxyalkyl groups, ($C_1$–$C_6$) alkylcarbonyl groups, formyl groups, trifluoro($C_1$–$C_6$)alkylcarbonyl groups, ($C_1$–$C_6$) alkylcarboxyl groups, carbamyl groups, N—($C_1$–$C_6$)alkylcarbamyl groups, N,N-di($C_1$–$C_6$)alkylcarbamyl groups, thiocarbamyl groups and $C_1$–$C_6$alkylsulfonyl groups and groups Z as defined above, and, when said amine is substituted with two groups, said two groups may optionally form, together with the nitrogen atom to which said two groups are commonly bonded, at least one ring chosen from 5- and 6-membered carbon-based rings and rings comprising at least one hetero atom;

(5) amino groups protected with at least one group chosen from ($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$)alkylamino($C_1$–$C_6$)alkylcarbonyl groups, N,N-di($C_1$–$C_6$)alkylamino($C_1$–$C_6$)alkylcarbonyl groups, ($C_1$–$C_6$)alkylcarboxyl groups, carbamyl groups, N—($C_1$–$C_6$)alkylcarbamyl groups, N,N-di($C_1$–$C_6$)alkylcarbamyl groups, $C_1$–$C_6$alkylsulfonyl groups, aminosulfonyl groups, N—Z-aminosulfonyl groups, $C_1$–$C_6$N-alkylaminosulfonyl groups, N,N-di($C_1$–$C_6$)alkylaminosulfonyl groups, thiocarbamyl groups, formyl groups, and groups Z as defined above wherein said linker D in said groups Z comprises at least one ketone functional group directly bonded to the nitrogen atom of said amino group;

(6) $C_1$–$C_6$aminoalkyl groups, wherein the alkyl is optionally substituted with at least one hydroxyl group;

(7) amino($C_1$–$C_6$)alkyl groups, wherein the alkyl is optionally substituted with at least one hydroxyl group and wherein said amino is substituted with one or two groups, which may be identical or different, chosen from alkyl groups, $C_1$–$C_6$monohydroxyalkyl groups, $C_2$–$C_6$polyhydroxyalkyl groups, ($C_1$–$C_6$) alkylcarbonyl groups, carbamyl groups, N—($C_1$–$C_6$) alkylcarbamyl groups, N,N-di($C_1$–$C_6$)alkylcarbamyl groups, ($C_1$–$C_6$)alkylsulfonyl groups, formyl groups, trifluoro($C_1$–$C_6$)alkylcarbonyl groups, ($C_1$–$C_6$) alkylcarboxyl groups, thiocarbamyl groups, and said groups Z as defined above, and, when said amino is substituted with two groups, said two groups may optionally form, together with the nitrogen atom to which said two groups are commonly bonded, at least one ring chosen from 5- and 6-membered carbon-based ring and 5- and 6-membered rings comprising at least one hetero atom; and provided that when two of $R'_1$, $R'_2$, and $R'_3$ simultaneously are a hydrogen atom, and when the other group $R'_1$, $R'_2$, and $R'_3$ is a group comprising a functional group chosen from amido and carboxyl functional groups, then said amido and carboxyl functional group is not directly bonded to the naphthol ring system;

and further excluding:

6-hydroxy-N,N,N-trimethyl-1-naphthalenemethanaminium chloride; and

[(2-hydroxy-1-naphthyl)methyl]trimethylammonium iodide.

* * * * *